(12) United States Patent
Kuntz et al.

(10) Patent No.: US 12,376,895 B2
(45) Date of Patent: Aug. 5, 2025

(54) IMPLANTS FOR TISSUE FIXATION AND FUSION

(71) Applicant: CUTTING EDGE SPINE LLC, Mineral Springs, NC (US)

(72) Inventors: Kyle Kuntz, Waxhaw, NC (US); Shyam Patel, Waxhaw, NC (US)

(73) Assignee: CUTTING EDGE SPINE LLC, Mineral Springs, NC (US)

( * ) Notice: Subject to any disclaimer, the term of this patent is extended or adjusted under 35 U.S.C. 154(b) by 0 days.

(21) Appl. No.: 19/037,351

(22) Filed: Jan. 27, 2025

(65) Prior Publication Data
US 2025/0169864 A1 May 29, 2025

Related U.S. Application Data

(63) Continuation of application No. 18/456,245, filed on Aug. 25, 2023, now Pat. No. 12,239,350, which is a
(Continued)

(51) Int. Cl.
*A61B 17/86* (2006.01)
*A61B 17/70* (2006.01)
(Continued)

(52) U.S. Cl.
CPC ............ *A61B 17/869* (2013.01); *A61B 17/70* (2013.01); *A61B 17/7055* (2013.01);
(Continued)

(58) Field of Classification Search
CPC ... A61B 17/869; A61B 17/70; A61B 17/7055; A61B 17/764; A61B 2017/00526;
(Continued)

(56) References Cited

U.S. PATENT DOCUMENTS 5,282,861 A   2/1994 Kaplan
5,417,692 A   5/1995 Goble et al.
(Continued)

FOREIGN PATENT DOCUMENTS

EP    2796104      10/2014
JP    2012511334    5/2012
(Continued)

OTHER PUBLICATIONS

Zimmer Trabecular Metal Dental Implant Brochure; trabecular metal.zimmerdental.com, 2012, Carlsbad, California.
(Continued)

*Primary Examiner* — Jessica Weiss
(74) *Attorney, Agent, or Firm* — McNees Wallace & Nurick LLC

(57) ABSTRACT

A fixation implant includes a head, a shank and a distal tip, and one or more of the head, shank and distal tip may be cannulated. The shank includes a threaded ingrowth portion extending from the head to the tapered distal tip that includes external threads, and at least one open network body extending along the length of the ingrowth portion. The open network body selected from one or a combination of a helix, an arrangement of trusses, a scaffold of open and interconnected pores, a porous framework of random open and interconnected pores, and combinations of these.

17 Claims, 14 Drawing Sheets

Related U.S. Application Data continuation of application No. 17/672,478, filed on Feb. 15, 2022, now Pat. No. 11,446,070, which is a continuation of application No. 17/183,330, filed on Feb. 23, 2021, now Pat. No. 11,771,482, which is a continuation of application No. 15/976,989, filed on May 11, 2018, now Pat. No. 10,993,754.

(60) Provisional application No. 62/505,257, filed on May 12, 2017.

(51) Int. Cl.
    *A61F 2/44* (2006.01)
    *A61B 17/00* (2006.01)
    *A61F 2/30* (2006.01)

(52) U.S. Cl.
    CPC .......... *A61B 17/864* (2013.01); *A61F 2/4455* (2013.01); *A61B 2017/00526* (2013.01); *A61F 2002/30593* (2013.01); *A61F 2002/30622* (2013.01); *A61F 2002/3085* (2013.01); *A61F 2002/3092* (2013.01); *A61F 2002/30985* (2013.01); *A61F 2002/30995* (2013.01)

(58) Field of Classification Search
    CPC ........... A61B 2017/30593; A61B 2017/30622; A61B 2017/3085; A61B 2017/3092; A61B 2017/30985; A61B 2017/30995
    USPC .................................................. 606/300–321
    See application file for complete search history.

(56) References Cited

U.S. PATENT DOCUMENTS

| | | | |
|---|---|---|---|
| 6,375,655 | B1 | 4/2002 | Zdeblick et al. |
| 6,960,216 | B2 | 11/2005 | Kolb et al. |
| 7,458,991 | B2 | 12/2008 | Wang et al. |
| 7,534,254 | B1 | 5/2009 | Michelson |
| 7,736,381 | B2 | 6/2010 | Biedermann et al. |
| 8,057,475 | B2 | 11/2011 | Michelson |
| 8,075,312 | B2 * | 12/2011 | Collins ................ A61C 8/0012 433/173 |
| 8,137,389 | B2 | 3/2012 | Biedermann et al. |
| 8,231,387 | B2 | 7/2012 | Salvi et al. |
| 8,414,654 | B1 | 4/2013 | Ganey |
| 8,430,930 | B2 | 4/2013 | Hunt |
| 8,864,839 | B2 | 10/2014 | Ganey |
| 8,899,982 | B2 | 12/2014 | Damstra et al. |
| 8,900,279 | B2 | 12/2014 | Assell et al. |
| 8,968,372 | B2 | 3/2015 | Biedermann et al. |
| 8,979,911 | B2 | 3/2015 | Martineau et al. |
| 9,095,396 | B2 | 8/2015 | Collins et al. |
| 9,179,954 | B2 | 11/2015 | Ganey |
| 9,421,108 | B2 | 8/2016 | Hunt |
| 9,468,483 | B2 | 10/2016 | Biedermann et al. |
| 9,545,317 | B2 | 1/2017 | Hunt |
| 9,636,226 | B2 | 5/2017 | Hunt |
| 9,662,157 | B2 | 5/2017 | Schneider et al. |
| 9,724,203 | B2 | 8/2017 | Nebosky et al. |
| 9,949,834 | B2 | 4/2018 | Pressacco |
| 9,987,065 | B2 | 6/2018 | De Lavigne Sainte Suzanne |
| 9,999,516 | B2 | 6/2018 | Hunt |
| 10,194,962 | B2 | 2/2019 | Schneider et al. |
| 10,285,816 | B2 | 5/2019 | Roby et al. |
| 10,321,940 | B2 | 6/2019 | Anderson et al. |
| 2006/0036253 | A1 | 2/2006 | Leroux et al. |
| 2006/0116679 | A1 | 6/2006 | Lutz et al. |
| 2006/0276788 | A1* | 12/2006 | Berry ................. A61B 17/7005 606/301 |
| 2007/0055244 | A1* | 3/2007 | Jackson ............. A61B 17/7028 606/86 A |
| 2007/0065779 | A1 | 3/2007 | Mangano |
| 2007/0162019 | A1 | 7/2007 | Burns et al. |
| 2009/0254126 | A1 | 10/2009 | Orbay et al. |
| 2009/0259261 | A1 | 10/2009 | Reiley |
| 2010/0042167 | A1* | 2/2010 | Nebosky ............... A61M 37/00 606/301 |
| 2010/0094292 | A1 | 4/2010 | Parrott |
| 2010/0094420 | A1 | 4/2010 | Grohowski, Jr. |
| 2010/0137990 | A1 | 6/2010 | Apatsidis et al. |
| 2010/0145393 | A1 | 6/2010 | Fallin et al. |
| 2011/0015684 | A1 | 1/2011 | Belcheva et al. |
| 2011/0060373 | A1 | 3/2011 | Russell et al. |
| 2011/0087296 | A1 | 4/2011 | Reiley et al. |
| 2012/0265256 | A1 | 10/2012 | Biedermann et al. |
| 2012/0271362 | A1* | 10/2012 | Martineau ................ B22F 7/008 470/9 |
| 2012/0323285 | A1 | 12/2012 | Assell et al. |
| 2013/0072933 | A1 | 3/2013 | Biedermann et al. |
| 2013/0123935 | A1 | 5/2013 | Hunt et al. |
| 2013/0178900 | A1 | 7/2013 | Fallin et al. |
| 2013/0226251 | A1* | 8/2013 | Chegini ............. A61B 17/8625 606/325 |
| 2013/0245763 | A1 | 9/2013 | Mauldin |
| 2014/0030675 | A1* | 1/2014 | Sanchez ............... A61C 8/0012 433/174 |
| 2014/0039565 | A1* | 2/2014 | Martineau ............ A61B 17/864 606/304 |
| 2014/0046379 | A1 | 2/2014 | Sweeney |
| 2014/0081339 | A1 | 3/2014 | Bowman et al. |
| 2014/0277461 | A1 | 9/2014 | Nebosky et al. |
| 2015/0105830 | A1 | 4/2015 | Biedermann et al. |
| 2015/0127057 | A1 | 5/2015 | Ganey |
| 2015/0209094 | A1* | 7/2015 | Anderson ............ A61B 17/864 470/10 |
| 2015/0250513 | A1* | 9/2015 | De Lavigne Sainte Suzanne ....... A61B 17/864 606/304 |
| 2015/0282946 | A1 | 10/2015 | Hunt |
| 2015/0313658 | A1 | 11/2015 | Kolb |
| 2016/0157908 | A1 | 6/2016 | Cawley et al. |
| 2016/0166301 | A1 | 6/2016 | Papangelou et al. |
| 2017/0095337 | A1 | 4/2017 | Pasini et al. |
| 2017/0216035 | A1 | 8/2017 | Hunt |
| 2018/0085230 | A1 | 3/2018 | Hunt |
| 2018/0092677 | A1 | 4/2018 | Peterson et al. |
| 2018/0214192 | A1 | 8/2018 | Roby et al. |
| 2018/0263669 | A1* | 9/2018 | Peterson ............. A61B 17/8605 |
| 2019/0159818 | A1 | 5/2019 | Schneider et al. |
| 2019/0239935 | A1 | 8/2019 | Willis et al. |
| 2021/0196333 | A1 | 7/2021 | Kuntz et al. |

FOREIGN PATENT DOCUMENTS

| | | |
|---|---|---|
| JP | 2014083354 | 5/2014 |
| JP | 2015509435 | 3/2015 |
| JP | 2016513572 | 5/2016 |
| JP | 2020519413 | 7/2020 |
| RU | 2150964 C1 | 6/2000 |
| RU | 2172146 C1 | 8/2001 |
| WO | 2001005325 | 8/2001 |
| WO | 2002034120 A2 | 5/2002 |
| WO | 2002038054 | 5/2002 |
| WO | 2006127392 A2 | 11/2006 |
| WO | 2008021474 A2 | 2/2008 |
| WO | 2008044011 A2 | 4/2008 |
| WO | 2008101932 A2 | 8/2008 |
| WO | 2009025884 | 2/2009 |
| WO | 2010002663 A1 | 1/2010 |
| WO | 2010019788 | 2/2010 |
| WO | 2010045116 A1 | 4/2010 |
| WO | 2010080511 A1 | 7/2010 |
| WO | 2011044697 A1 | 4/2011 |
| WO | 2011086529 A1 | 7/2011 |
| WO | 2012171011 A1 | 12/2012 |
| WO | 2013006778 A2 | 1/2013 |
| WO | 2013067528 A1 | 5/2013 |
| WO | 2013077897 A1 | 5/2013 |
| WO | WO-2013091392 A1 * | 6/2013 ......... A61B 17/7032 |
| WO | 2013134678 A1 | 9/2013 |
| WO | 2013150369 A1 | 10/2013 |

(56) References Cited

FOREIGN PATENT DOCUMENTS

| | | |
|---|---|---|
| WO | 2014068259 A1 | 5/2014 |
| WO | 2014143719 A1 | 9/2014 |
| WO | 2014145529 A1 | 9/2014 |
| WO | 2015164982 A1 | 11/2015 |
| WO | 2016099620 A1 | 6/2016 |
| WO | 2017066518 | 4/2017 |
| WO | 2017096199 A1 | 6/2017 |
| WO | 2017201371 A1 | 11/2017 |
| WO | 2018100250 A1 | 6/2018 |
| WO | 2018140375 A1 | 8/2018 |
| WO | 2018209177 | 11/2018 |
| WO | 2018215756 A1 | 11/2018 |
| WO | 2019050392 A1 | 3/2019 |
| WO | 2019122473 A1 | 6/2019 |
| WO | 2019126199 A1 | 6/2019 |

OTHER PUBLICATIONS

PCT Notification of Transmittal of the International Search Report and the Written Opinion of the ISR issued for PCT/US2018/032215 dated Sep. 6, 2018.
Examination Report issued to Australian counterpart Application No. 2018265427 dated Jul. 27, 2023.
Examination Report issued to Australian counterpart Application No. 2018265427 dated Apr. 5, 2023.
Extended Search Report issued to European counterpart Application No. 18798786.2 dated Jan. 27, 2021.

* cited by examiner

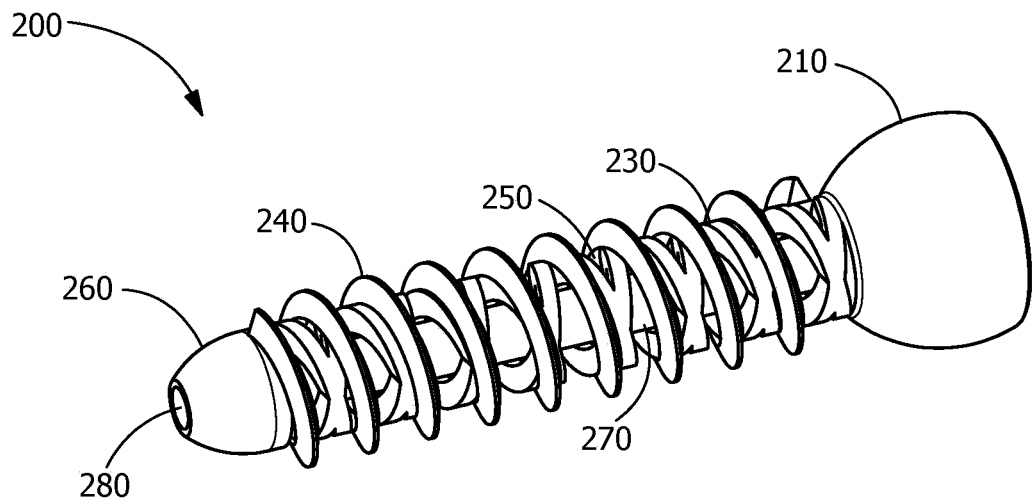
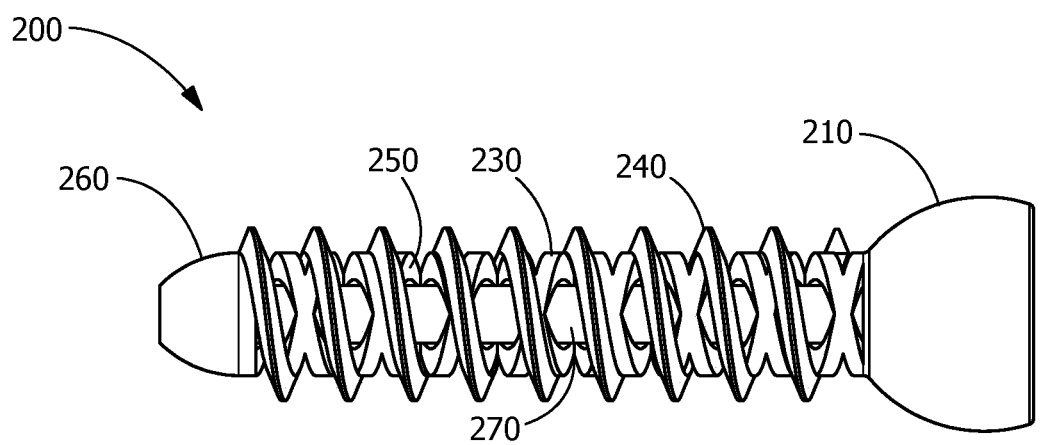
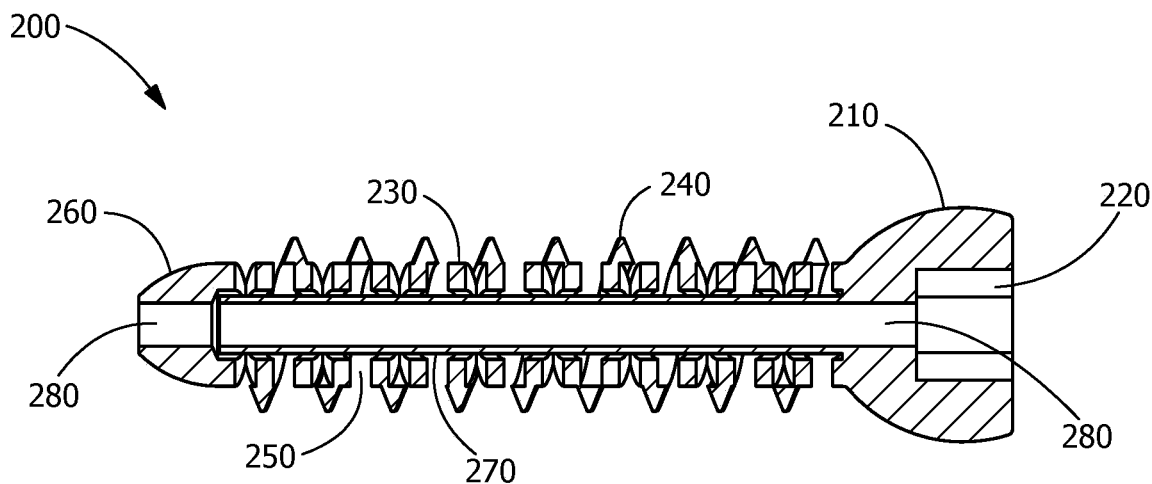
FIG. 2

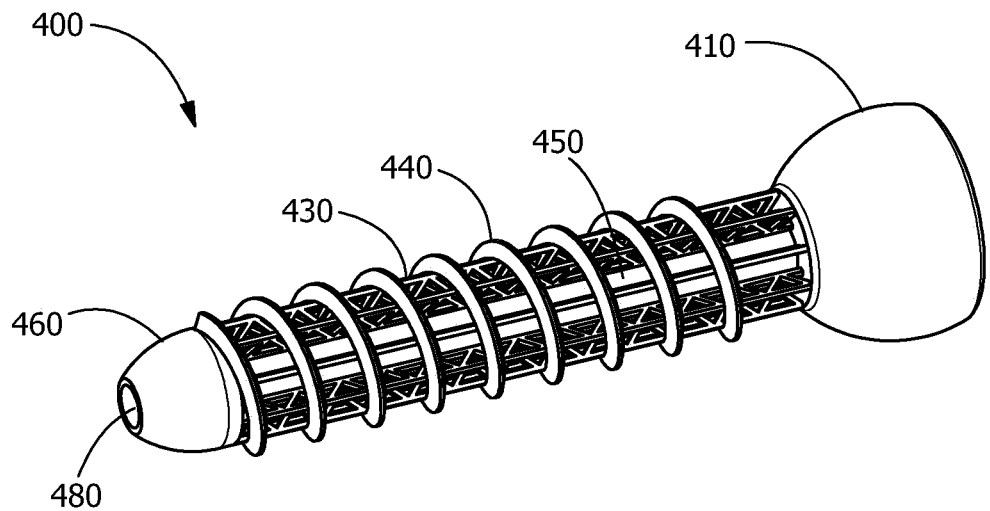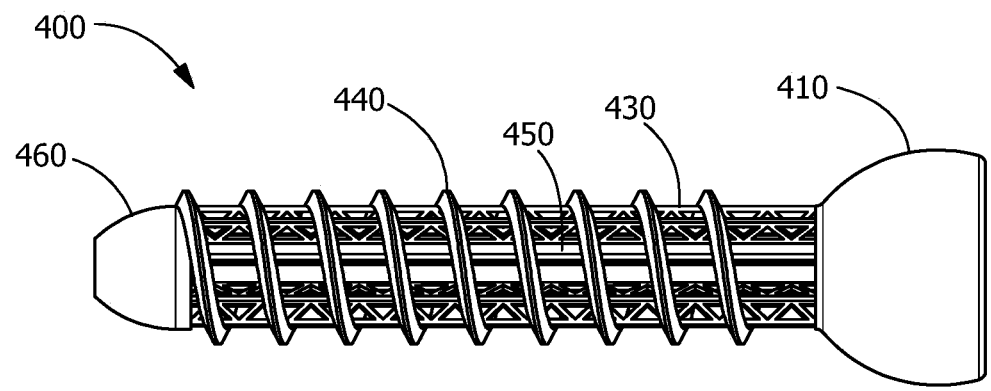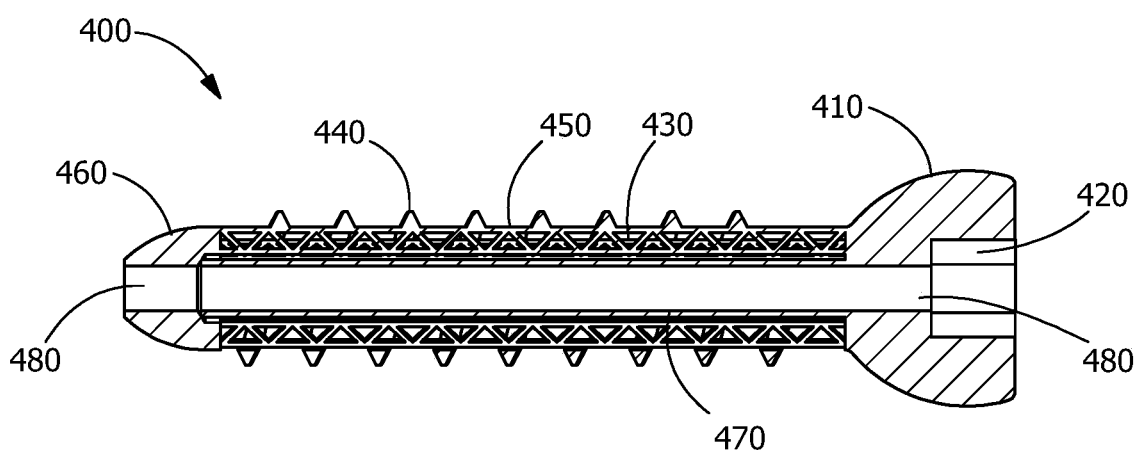
FIG. 4

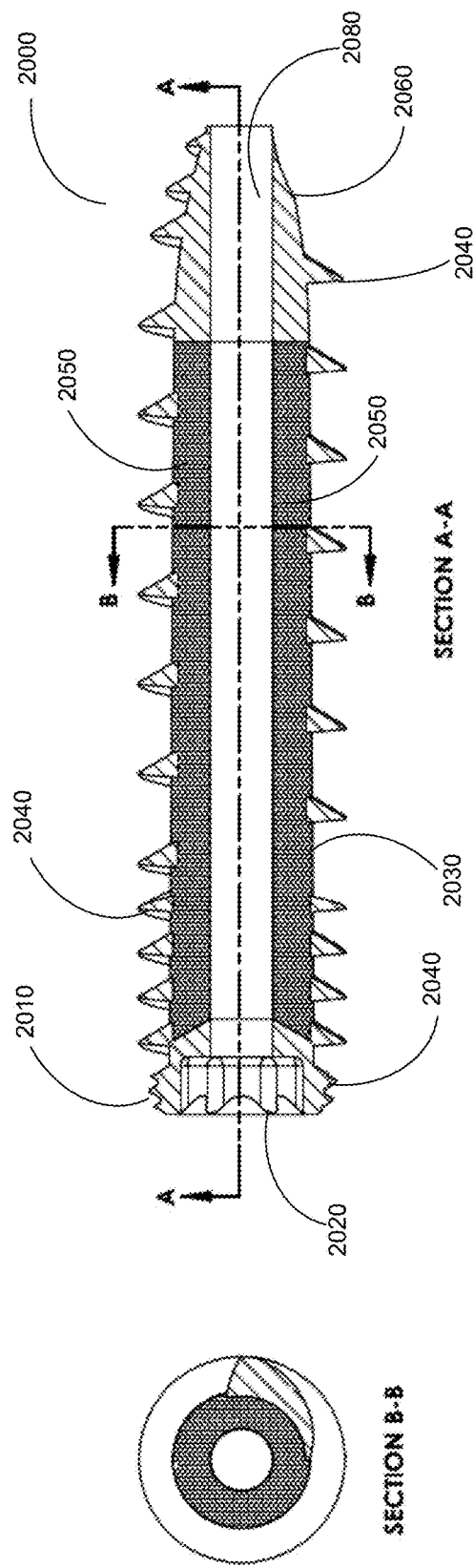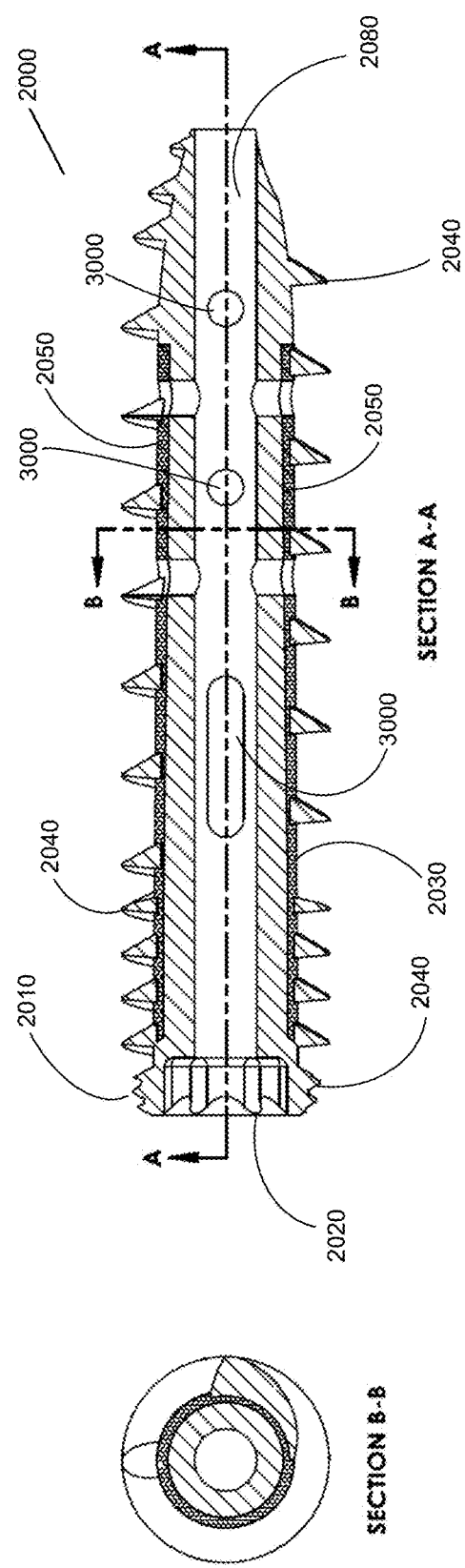
FIG 12
FIG 13

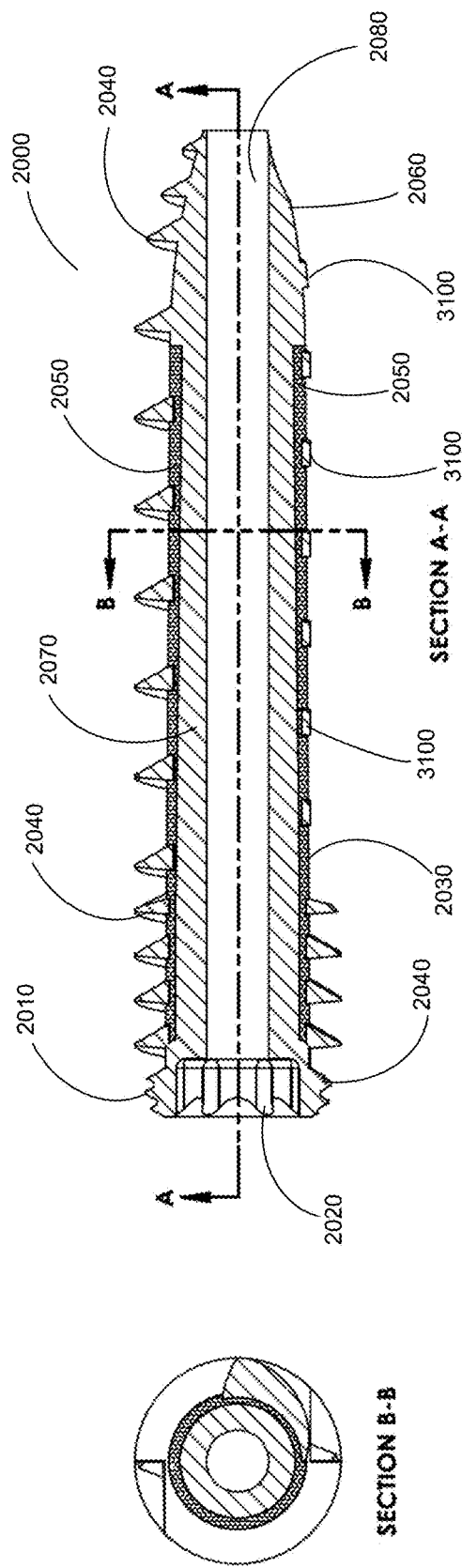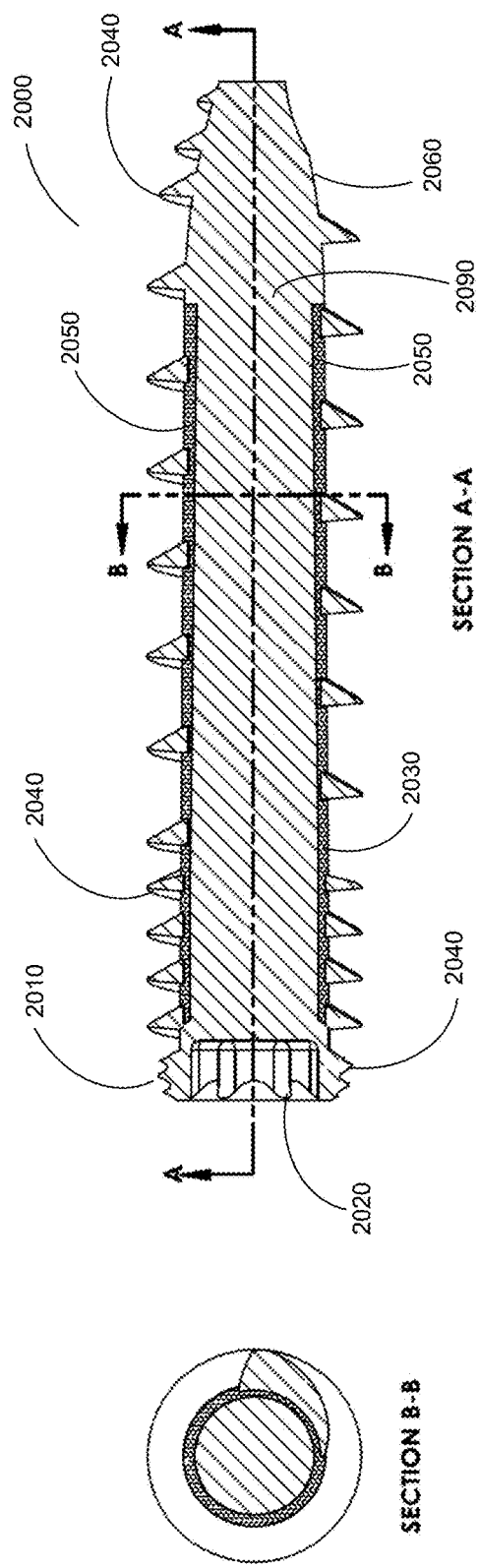

IMPLANTS FOR TISSUE FIXATION AND FUSION

RELATED APPLICATION

This application is a continuation of U.S. Nonprovisional application Ser. No. 18/456,245 filed Aug. 25, 2023, which is a continuation of U.S. Nonprovisional application Ser. No. 17/672,478 filed Feb. 15, 2022 which has issued as U.S. Pat. No. 11,446,070 dated Aug. 25, 2023, which is a continuation of U.S. Nonprovisional application Ser. No. 17/183,330 filed Feb. 23, 2021 which has issued as U.S. Pat. No. 11,771,482 dated Oct. 3, 2023, which is a continuation of U.S. Nonprovisional application Ser. No. 15/976,989 filed on May 11, 2018 which has issued as U.S. Pat. No. 10,993,754 dated May 4, 2021, which claims the benefit under 35 U.S.C. § 119 (e) to U.S. Provisional Application Ser. No. 62/505,257 filed May 12, 2017, the entirety of which is incorporated herein by reference.

FIELD

The present application describes various exemplary devices and surgical techniques for securing tissue, particularly bone tissue, and more particularly in some examples, bone tissue in the spine associated with the sacroiliac joint.

DESCRIPTION OF THE RELATED ART

In the context of orthopedics, a variety of conditions, including injuries, degeneration, and congenital abnormalities, can present the need for interventional implants and surgical techniques to achieve one or more of bone repair, stabilization, and correction. Conventional procedures have been developed using mechanical implants, for example to straighten or otherwise stabilize joints, secure fragments of fractured bones, and secure and stabilize successive vertebrae, sacral iliac bones, and other adjacent bones in a fixed position. These implants include bone screws, anchors, rods, bands, plates, and combinations of these devices that are comprised of one or a combination of metal, polymers, biomaterials and other biologically acceptable materials.

In one example, fixation and fusion is needed for addressing sacroiliac dysfunction or instability that occurs in the sacroiliac joint. In a typical subject, the sacroiliac joint spans between the sacrum bone and ilium bone and has a natural degree or motion, or nutation, of one to two degrees. In the case of injury to the joint, the typically small range of motion can be exaggerated and lead to hypermobility, an often difficult condition to diagnose because it involves lower back and leg pain which are symptoms that are common with other spinal and orthopedic problems. Once diagnosed, there are surgical options for fixation and fusion of the sacroiliac joint. But due to the natural movement of the joint, typical bone screw type implants can be vulnerable to rotation and ultimate failure.

Accordingly, there is a need for implant devices that can straighten or otherwise stabilize joints, secure fragments of fractured bones, and secure and stabilize successive vertebrae, sacral iliac bones, and other adjacent bones in a fixed position. Such improved devices are needed for the maintenance of stability of securement of the bones, for example prevention of rotation of one or both of bone and implant that can destabilize fixation and cause movement or migration of the joined bone, of the implant, and combinations of these. Thus, applications would include correcting instability and hypermobility in fixated joints, and providing resistance to rotational and pull out failures in order to achieve the desirable degree of fusion across a joint, across joined portions of bone, and in the context of implants secured to bone. In some particular applications, there is a need for devices that enhance and provide more secure fixations of the sacroiliac joint, including greater bone purchase and retention, and features for enhanced tissue integration.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 2 shows yet another embodiment of a fixation implant characterized in having an external thread over an open helical body having an solid-walled inner cylindrical through channel, and shown in oblique, side and side cross sectional views.

FIG. 4 shows another embodiment of a fixation implant characterized in having an external thread over an open organized truss arrangement with a solid-walled inner cylindrical through channel, and shown in oblique, side and side cross sectional views.

FIG. 12 shows an embodiment of a fixation implant in side cross sectional view that is cannulated with a wall formed of a framework of random open and interconnected pores along a portion of the length of the shank, the outer framework of random open and interconnected pores bounded on the exterior by an outer thread, and a threaded cylindrical head and threaded self-tapping distal tip each lacking an outer framework of random open and interconnected pores, each of the cylindrical head, the distal tip, the proximal portion of the shank and a central to distal portion of the shank having a different thread.

FIG. 13 shows an embodiment of a fixation implant in side cross sectional view that is cannulated with a solid-walled inner cylindrical through channel and an outer framework of random open and interconnected pores along a portion of the length of the shank, the outer framework of random open and interconnected pores bounded between the inner solid wall and an outer thread, and a threaded cylindrical head and threaded self-tapping distal tip each lacking an outer framework of random open and interconnected pores, the shank having circular and slotted fenestrations arranged along the its length, and each of the cylindrical head, the distal tip, the proximal portion of the shank and a central to distal portion of the shank having a different thread.

FIG. 14 shows an embodiment of a fixation implant in side cross sectional view that is cannulated with a solid-walled inner cylindrical through channel and an outer framework of random open and interconnected pores along a portion of the length of the shank, the outer framework of random open and interconnected pores bounded between the inner solid wall and an outer thread, and a threaded cylindrical head and threaded self-tapping distal tip each lacking an outer framework of random open and interconnected pores, the distal tip, the proximal portion of the shank and a central to distal portion of the shank having a different thread, and the shank threading being discontinuous/interrupted at regular intervals along the length of the threaded portion of the shank.

FIG. 15 shows an embodiment of a fixation implant in side cross sectional view that is un-cannulated with a solid-walled center and an outer framework of random open and interconnected pores along a portion of the length of the shank, the outer framework of random open and interconnected pores bounded between the inner solid wall and an outer thread, and a threaded cylindrical head and threaded self-tapping distal tip each lacking an outer framework of random open and interconnected pores, each of the cylindrical head, the distal tip, the proximal portion of the shank and a central to distal portion of the shank having a different thread.

Figure 1:
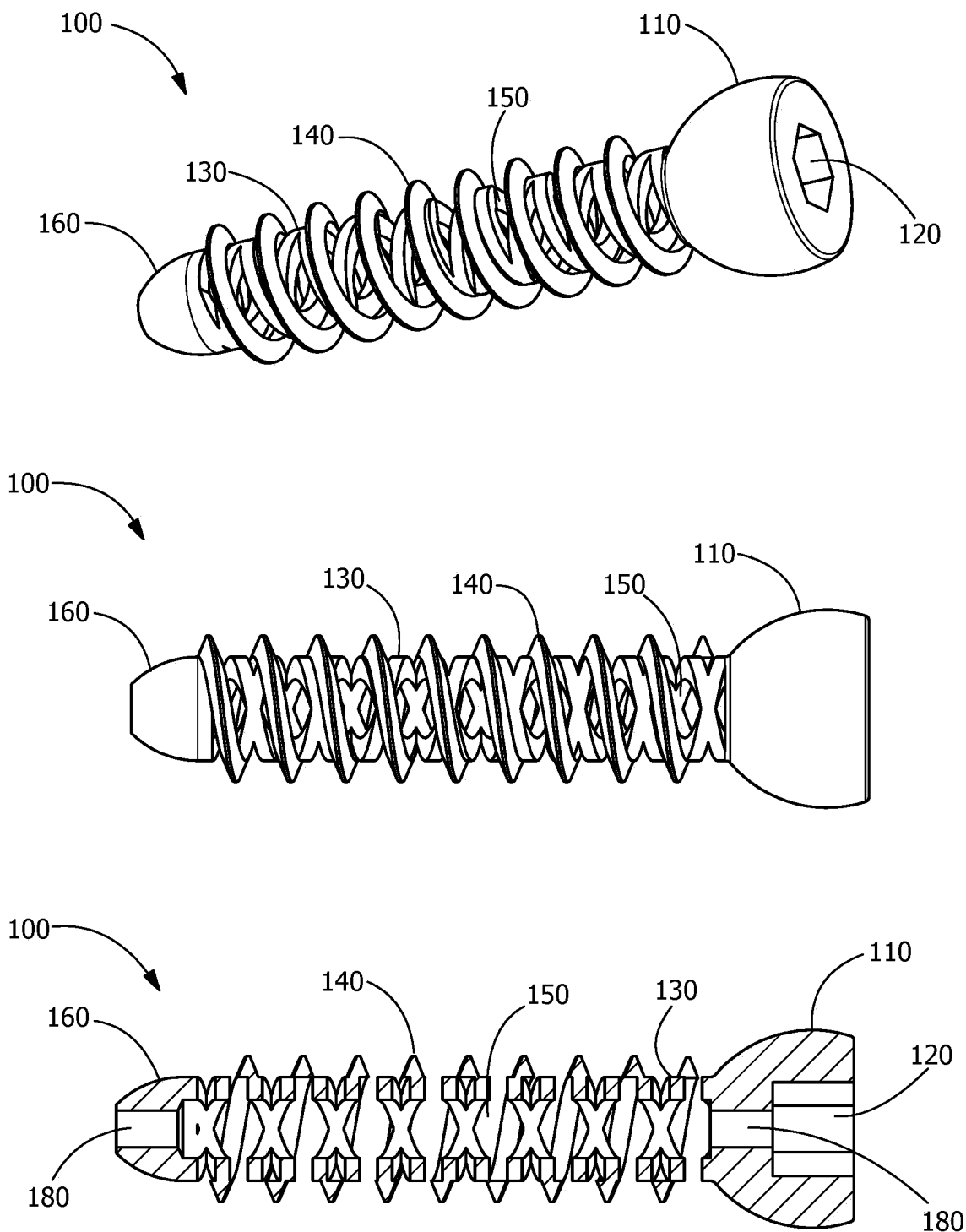
FIG. 1 shows another embodiment of a fixation implant characterized in having an external thread over an open helical body, and shown in oblique, side and side cross sectional views.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community, and generally, any and all terms providing spatial references to anatomical features shall have meaning that is customary in the art. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front, and the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced.

"Patient" is used to describe an animal, preferably a human, to whom treatment is administered, including prophylactic treatment with the compositions of the present invention. "Concave" is used herein to describe an indented surface without reference to the specific shape of the indented surface. As non-limiting examples, the concave face may be tubular with a round cross section, oval cross section, square cross section, or rectangular cross section.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, some references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

The present application describes various embodiments of devices for joint and other bone fixation. In some particular embodiments, devices for fixation of the sacroiliac joint are provided. It will be appreciated that the examples and drawings, as shown herein, may be described in reference to use in applications for sacroiliac joint fusion, though the devices as disclosed herein may be used in any of a variety of other orthopedic applications and may be used alone, or as an adjunct to devices used for other fixation or correction, such as, for example, in spine fusion surgery, to help hold other implants in place.

Fixation Implants

In accordance with various embodiments, the invention provides a fixation implant that comprises fixation member having a proximal head and a shank with a distal tip. The fixation implant is advantageously used for accomplishing fixation of tissue, such as bone tissue, in some examples including adjacent bones at a joint such as the sacroiliac joint, or bone fracture fragments. The implant provides enhanced resistance to rotational motion, rotational migration and pull out as compared with other fixation member designs, this advantage owing to one or more of increased bone engagement surface, enhanced opportunity for osseointegration, and enhanced bone purchase as a result of the extensively enhanced surface area of the three-dimensional open structure of at least a portion of the implant. The fixation implant includes one or more of head and shank features modeled to resemble the open and interconnected porosity features of trabecular bone in a variety of different embodiments.

In accordance with the various embodiments, the shank of the fixation member includes one or more openings or slots through the shank, in some embodiments arranged as a plurality around the periphery of the shank, to further enhance bony ingrowth. The openings are referred to herein as an open core and are formed of an open network body that provides a framework comparable to that of trabecular bone. As further described herein, an open core may be formed within any of the head and the shank portions and comprises at least one open network body. In some particular embodiments, the shank portion includes an open core comprising an open network body and one or both of the head and distal tip are solid (i.e., do not include an open network body) and may include a through cannula. In some embodiments, an open network body may be selected from one or a combination of: at least one elongate helix; an organized arrangement of trusses; a random arrangement of trusses; a framework or scaffold of random open and interconnected pores; and, a porous framework of random open and interconnected pores. Thus, in some embodiments, the entire fixation implant may have an open core formed of at least one type of open network structure or combinations thereof.

In accordance with the various embodiments, the open network body of the fixation implant allows materials to move into or out of the open core of the shank, the materials including bone fillers and other materials that would encourage bony ingrowth. Of course, in some such embodiments, the fixation implants may be provided without any filler materials. In accordance with the various embodiments, all or any portion of the fixation implant may be formed of one or more of a metal and a polymer. In particular, the head, the shank, the open core and the distal tip may be partially or completely formed from one or a combination of materials selected from metal and a polymer. In some particular examples, all or a portion of the materials forming the trabecular body may be osseo-inductive, selected from materials such as titanium, or others, and in some embodiments, the entire fixation implant may have an open core formed of a metal, a polymer, or combinations of these with or without other additive materials such as hydroxyapatite, and the open core may be open or closed.

An open network body has an open and interconnected matrix that allows communication between all bony material 360 degrees around the bone to optimize complete bony integration. This is advantageous over existing screw designs that have one or a series of fenestrations in an otherwise solid body of the shank, such fenestrations providing incomplete (i.e., less than 360 degree) engagement with bone. The three-dimensional structures of the open network body can provide greater support and stress distribution as compared to through holes and other fenestrations in the body of the shank of a conventional hollow screw that is designed to encourage bony ingrowth. Similar to the function of the trabeculae in bone, the open network structures of the open network body can allow for more even stress distribution than fenestrations would permit while also presenting open portions for bony ingrowth circumferentially at all points of circumferential contact with bone.

Referring now to FIG. 1, an exemplary embodiment of a fixation member 100 is shown. The fixation member 100 is characterized in having a head 110 and a shank 130 with an external thread 140 over an open core comprising a helical body 150 having the shape of a helix along the length of the shank 130, the fixation member 100 generally resembling the overall shape of a bone screw. According to the various embodiments, the open core as shown in FIG. 1 in the form of a helical body 150 provides an example of an open network body according to the invention that is adapted to encourage bony growth through the implant when it is fixed in bone. As shown in FIG. 1 and the other embodiments, the thread 140 is disposed on and integral with the helical body 150 forming the open network body of the open core, such that the helical body 150 is at least partially visible along the length of at least a portion of the shank 130 in the gaps between the thread 140, providing access into the helical body 150 to allow tissue infiltration and bony ingrowth therein.

Figure 7:
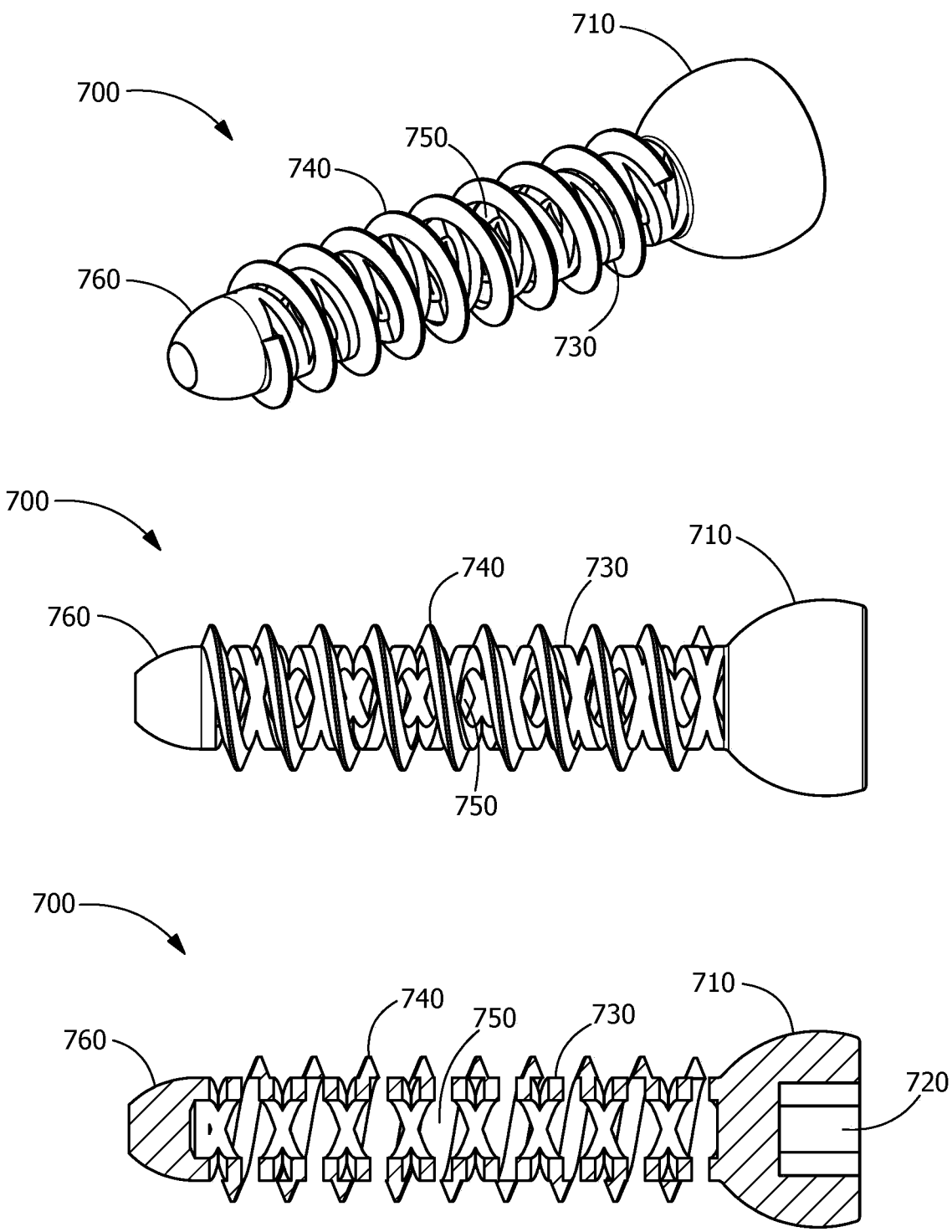
FIG. 7 shows another embodiment of a fixation implant characterized in having an external thread over an open helical body, wherein the implant is not cannulated and is shown in oblique, side and side cross sectional views.

Referring again to FIG. 1, in the exemplified embodiment, the fixation implant 100 includes a proximal head 110 that has a generally spherical in shape and comprises a center through cannula 180 that passes from the head 110 through the distal tip 160, and a tool recess 120 for engaging a driving instrument. In alternate embodiments, the head shape may be generally hemispherical, generally cylindrical, generally conical, and generally frustoconical. Each of the head 110 and distal tip 160 is cannulated and otherwise solid (i.e., it is not formed of an open network). In alternate embodiments, one or more of the distal tip 160 and the head 110 may be non-cannulated and solid, or may be cannulated and partially or entirely formed from one of a solid and an open network. Referring now to FIG. 7-FIGS. 9A and B, as shown in alternate depicted embodiments, for example as shown in FIG. 7, the head 710 and distal tip 760 are solid (not cannulated).

The exemplified fixation implant 100 includes a shank 130 having a length defined between the proximal head 110 and a distal tip 160 and a shape that is generally cylindrical that does not taper from proximal to distal, with a distal tip 160 that is a tapered frustoconical shape. In alternate various embodiments, the shank shape is selected from generally cylindrical, generally conical and generally frustoconical. It will be appreciated that the shape and proportions of the implant are not intended to be limiting and that the relative dimensions of each of the head, shank and distal tip portions of the various embodiments may vary. In the various alternate embodiments, all or only a portion of the shank 130 may have one or more an external thread 140 arranged around the open core along the length of the shank 130.

In the various embodiments according to the disclosure, the open core is formed with an open network structure selected from one or a combination of: at least one elongate helix; an organized arrangement of trusses; a random arrangement of trusses; a framework or scaffold of random open and interconnected pores; and, a porous framework of random open and interconnected pores. Further, the open core may be open in its center (whether or not one or both of the head and the distal tip are cannulated), or it may be solid, or it may include an open network structure as described herein above, or it may comprise a solid inner wall, such as a cylindrical wall, or a fenestrated wall, or a combination of these. As briefly described herein, each of FIG. 1, FIG. 3, FIG. 5, FIG. 6 and FIG. 7 depicts a fixation implant in which the open core has an open center (where FIG. 7 is the one example in which the head and the distal tip are not cannulated), and, each of FIG. 2 and FIG. 4 depicts a fixation implant in which the open core includes at its center a solid cylindrical wall that is cannulated, and FIG. 8 and FIGS. 9A and B each depict fixation implants in which the open core has a center that is continuously filled with the open network, and in which the head and the distal tip are not cannulated.

It will be appreciated by one of ordinary skill in the art that while each of the depicted embodiments as shown in the drawings include various combinations of the features that include a head and a distal tip and a shank comprising one or open network bodies, there are numerous possible embodiments having combinations of features that are not shown in the drawings. Thus, in various alternate examples, the fixation implant may have any one or more of the following configurations along at least a portion of its length between the head and the distal tip, from proximal to distal: a through cannula surrounded by an open network body with exterior threading; a through cannula surrounded by a solid or fenestrated wall that is surrounded by an open network body with exterior threading; a solid wall that is surrounded by an open network body with exterior threading; and, a continuous open network body with exterior threading. Thus, FIG. 1 is an example of a fixation implant that has a through cannula from the proximal head portion through the distal tip, each of the proximal head portion and tip being otherwise solid (not an open network) and the shank comprises a void (the through cannula) surrounded by an open network body.

Referring now to FIG. 2, yet another embodiment of a fixation implant 200 is shown being characterized in having a shank 230 comprising an external thread 240 over an open core, the open core comprising a helical body 250 having the shape of a helix along the length of the shank 230, the helical body 250 having within it a solid-walled inner cylindrical through channel 270. In the depicted embodiment, each of the head 210 and the distal tip 260 are cannulated 280, and the head 210 includes a tool recess 220 for engaging a driving instrument.

Figure 3:
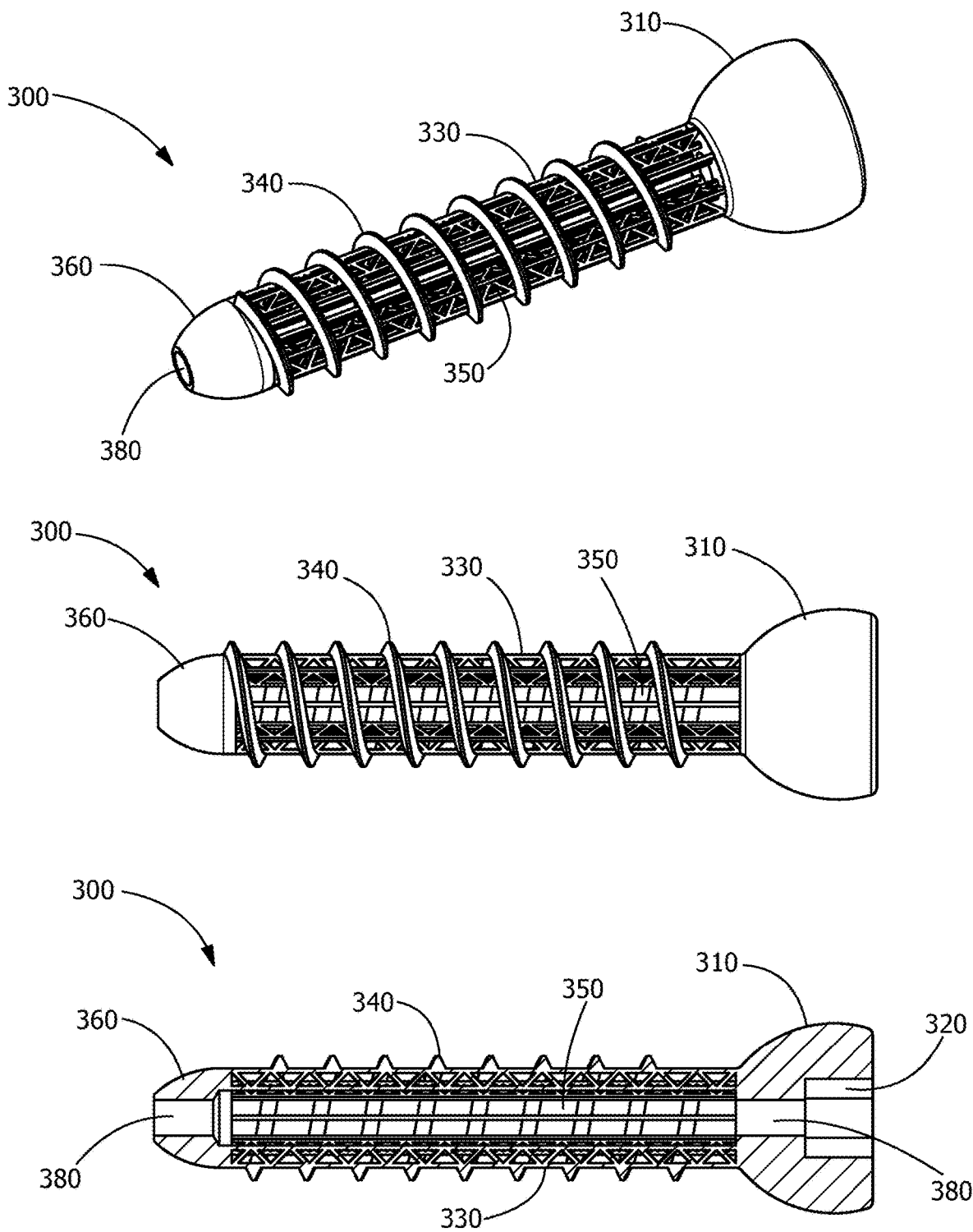
FIG. 3 shows yet another embodiment of a fixation implant characterized in having an external thread over an open organized truss arrangement, and shown in oblique, side and side cross sectional views.

Referring now to FIG. 3, yet another embodiment of a fixation implant 300 is shown being characterized in having a shank 330 comprising an external thread 340 over an open core, the open core comprising an organized truss body 350. In the depicted embodiment, each of the head 310 and the distal tip 360 are cannulated 380, and the head 310 includes a tool recess 320 for engaging a driving instrument.

Referring now to FIG. 4, yet another embodiment of a fixation implant is shown having a shank 430 comprising an external thread 440 over an open core, the open core comprising an organized truss body 450 that has a solid-walled inner cylindrical through channel 470. In the depicted embodiment, each of the head 410 and the distal tip 460 are cannulated 480, and the head 410 includes a tool recess 420 for engaging a driving instrument.

Figure 5:
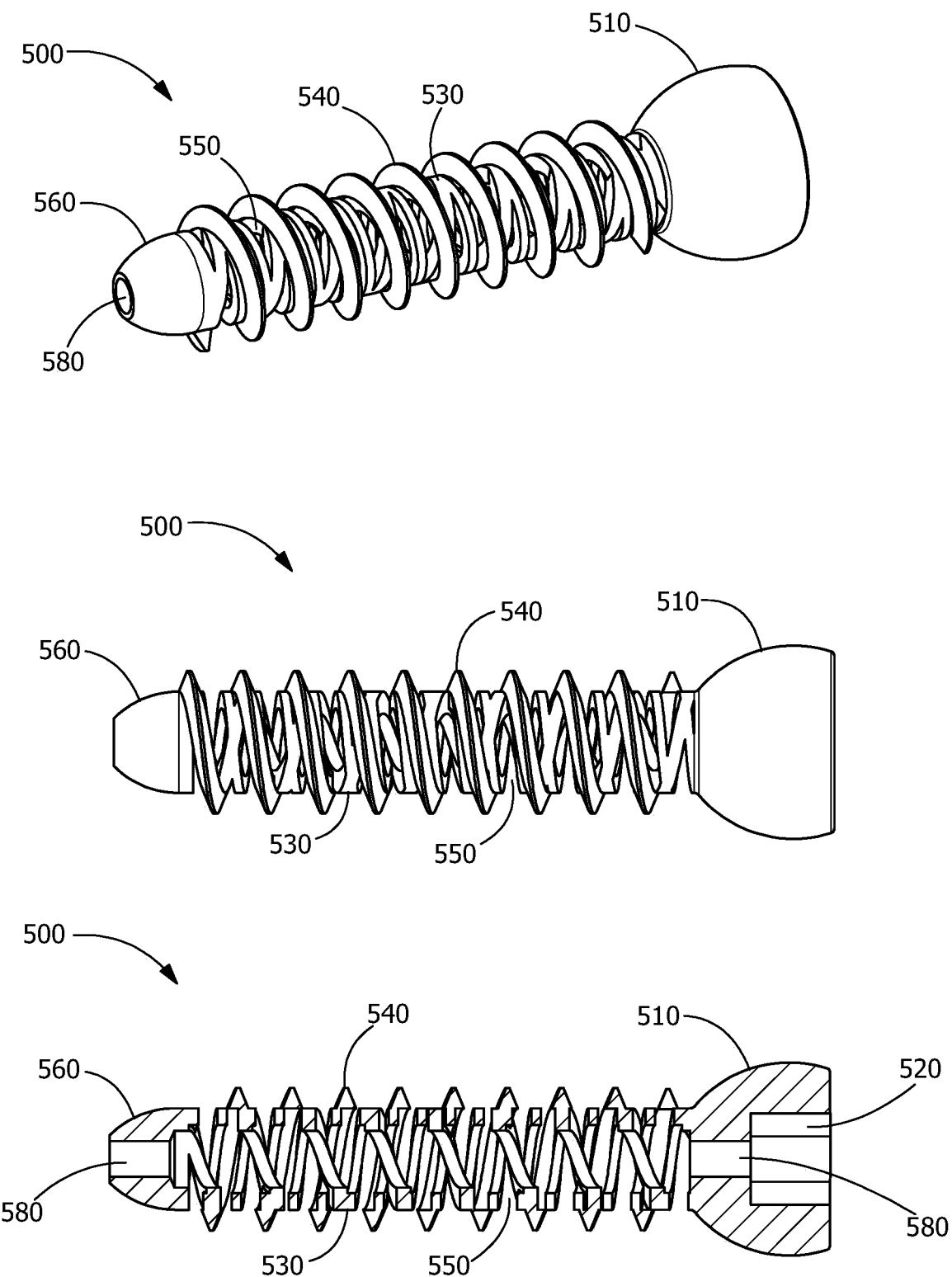
FIG. 5 shows another embodiment of a fixation implant characterized in having an external thread over an open helical body that includes two helices having different pitches, and shown in oblique, side and side cross sectional views.

FIG. 5 shows yet another embodiment of a fixation implant 500, the fixation implant 500 having a shank 530 characterized in having an external thread 540 over an open core comprising a dual helical body 550 that comprises two entwined helices, each helix having a different pitch. In the depicted embodiment, each of the head 510 and the distal tip 560 are cannulated 580, and the head 510 includes a tool recess 520 for engaging a driving instrument.

Figure 6:
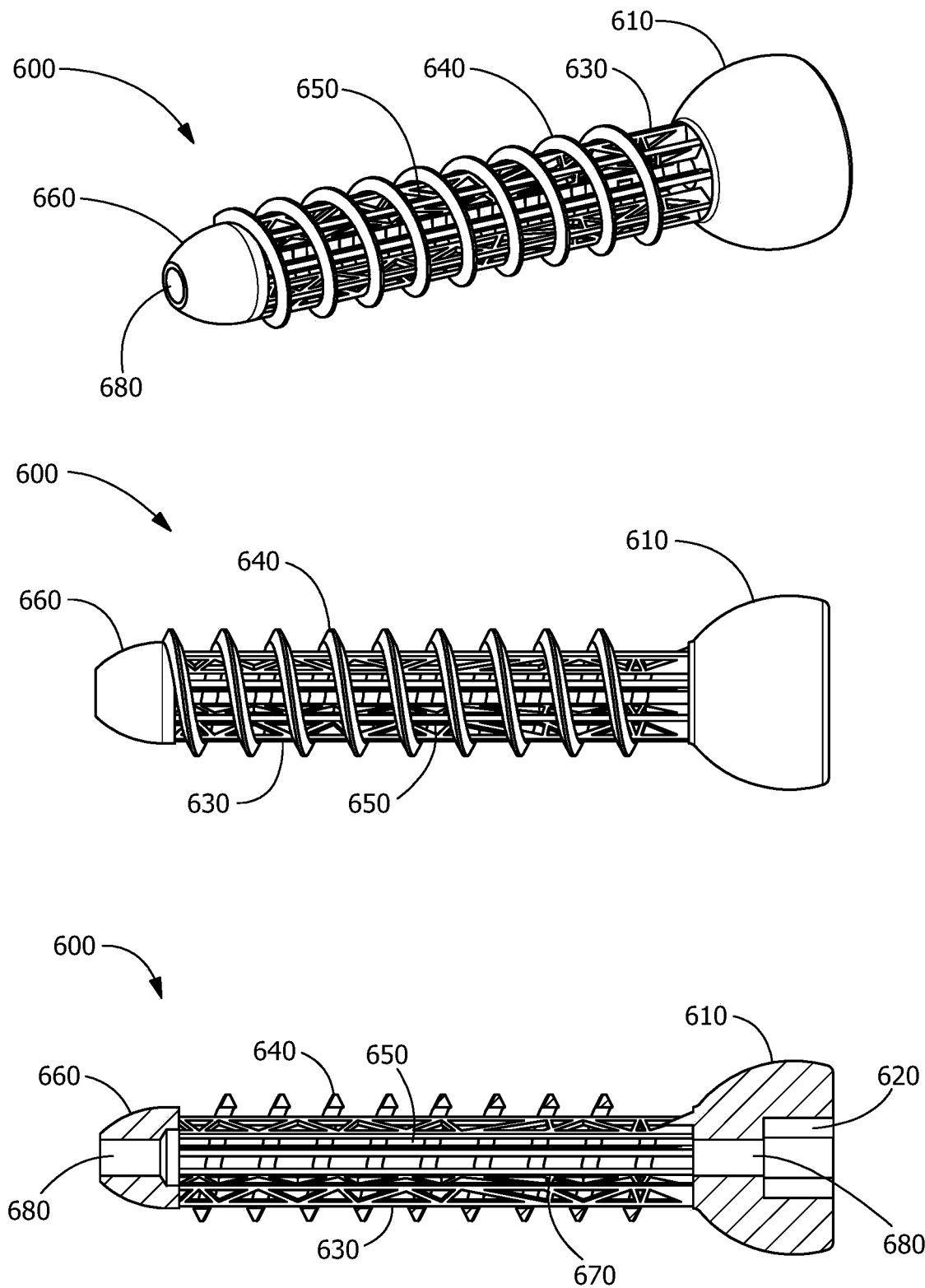
FIG. 6 shows another embodiment of a fixation implant characterized in having an external thread over an open disorganized truss arrangement with a fenestrated solid-walled inner cylindrical through channel, and shown in oblique, side and side cross sectional views.

Referring now to FIG. 6, yet another embodiment of a fixation implant 600 is shown being characterized in having a shank 630 having an external thread 640 over an open core comprising a disorganized truss body 650 with a solid-walled inner cylindrical through channel 670 that is fenestrated along its length and open to the threading as shown in the lower panel of FIG. 6. In the depicted embodiment, each of the head 610 and the distal tip 660 are cannulated 680, and the head 610 includes a tool recess 620 for engaging a driving instrument.

Referring now to FIG. 7, yet another embodiment of a fixation implant 700 is shown being characterized in having a shank 730 having an external thread 740 over an open (containing a void) helical body 750, where in the depicted embodiment, each of the head 710 and the distal tip 760 are not cannulated, and the head 710 includes a tool recess 720 for engaging a driving instrument.

Figure 8:
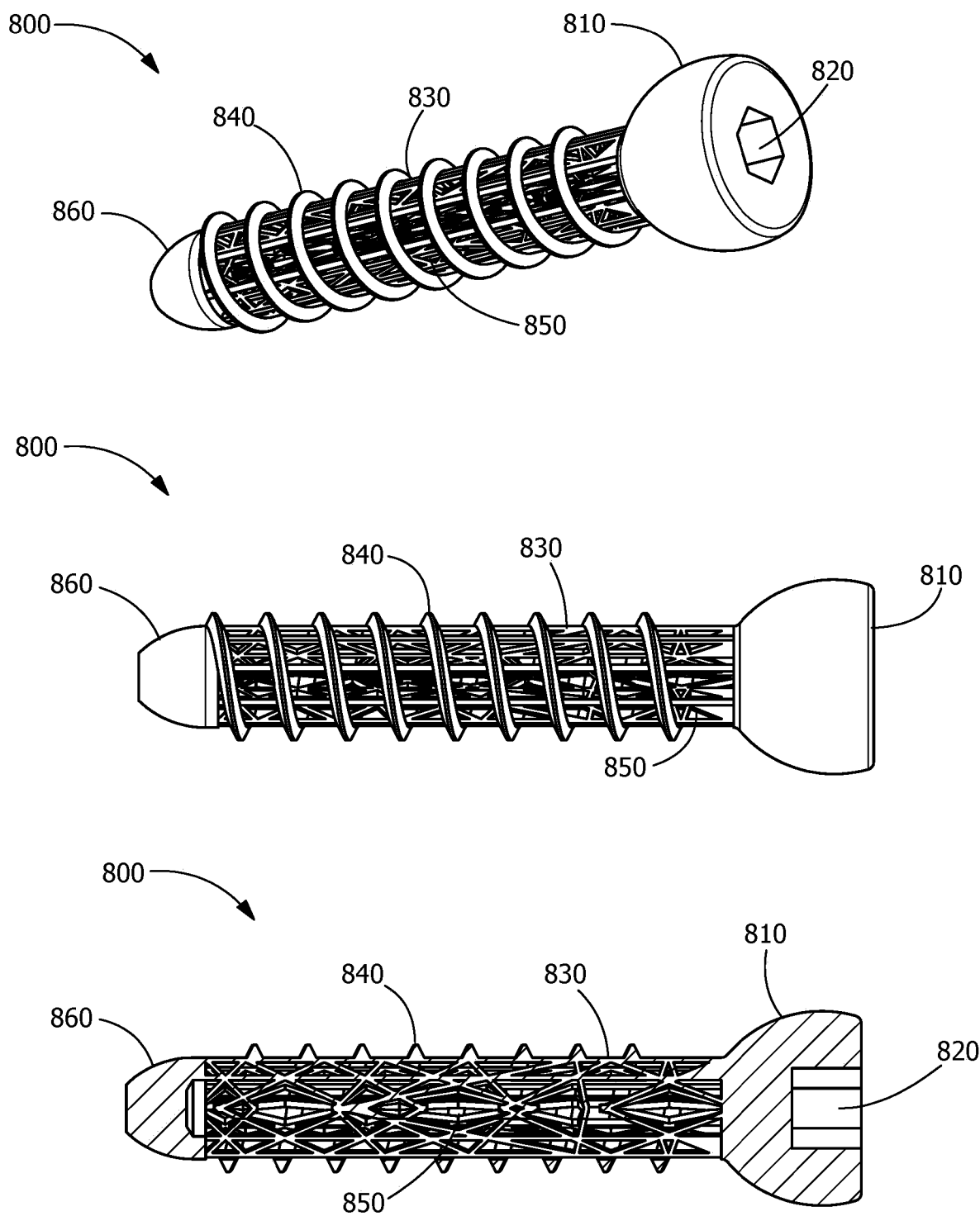
FIG. 8 shows another embodiment of a fixation implant characterized in having an external thread over an open and continuous disorganized truss arrangement wherein the implant is not cannulated and is shown in oblique, side and side cross sectional views.

Referring now to FIG. 8, yet another embodiment of a fixation implant 800 is shown being characterized in having a shank 830 having an external thread 840 over an open and continuous disorganized truss body 850 wherein the shank 830, the head 810 and the distal tip 860 are not cannulated, and the head 810 includes a tool recess 820 for engaging a driving instrument.

Figure 9A:
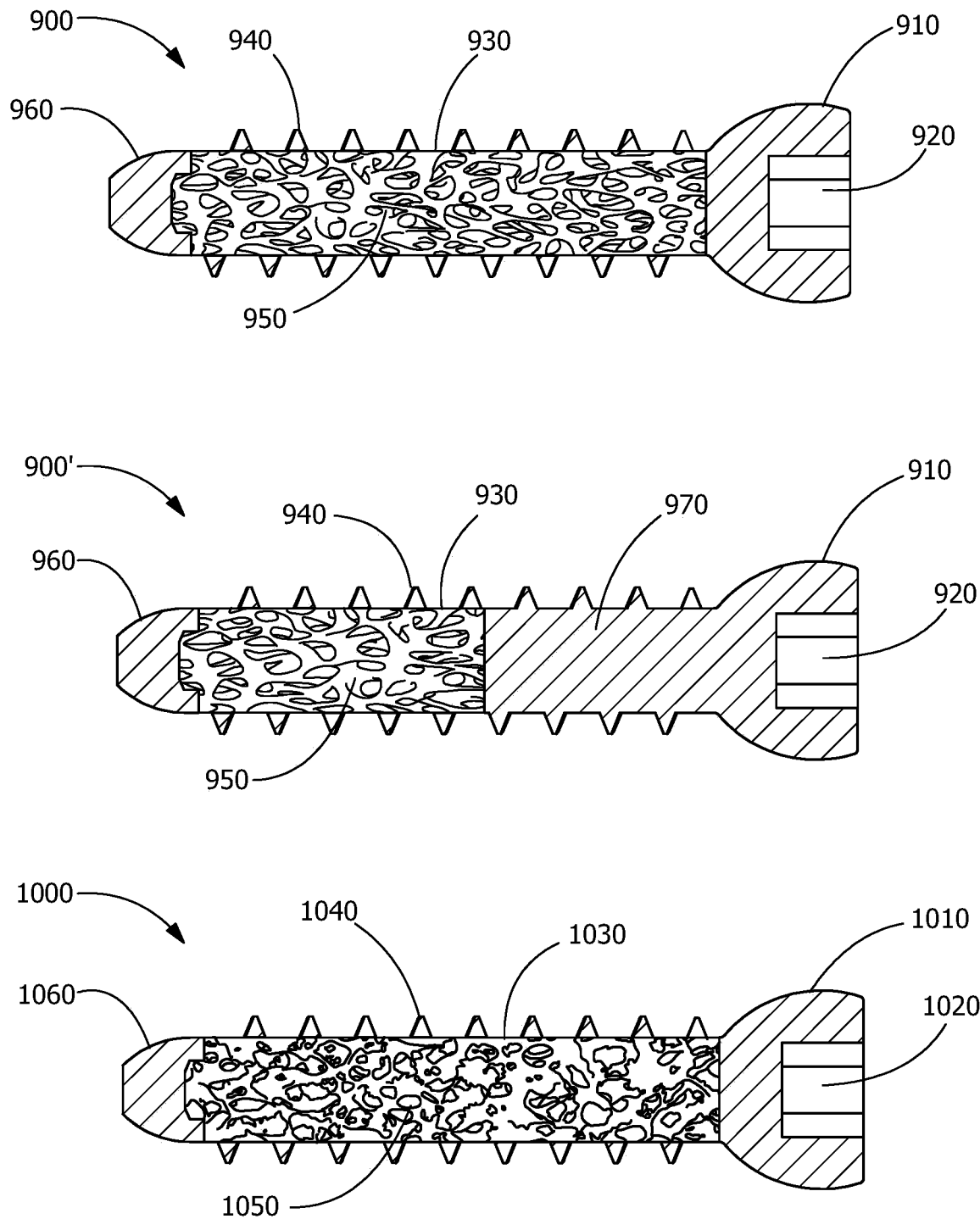
FIG. 9A shows three alternate embodiments of a fixation implant, the uppermost image depicting an non-cannulated implant having exterior threading and an interior framework of random open and interconnected pores, shown in a side cross sectional view; the middle image depicting a variation of the fixation member of the upper image that is only partially formed with the interior framework, shown in a side cross sectional view; and, the third and bottom image depicting an alternate embodiment of an non-cannulated implant having exterior threading and a porous interior framework of random open and interconnected pores, shown in a side cross sectional view.

Referring now to FIG. 9A, three alternate embodiments of a fixation implant are shown. Referring to the top image of FIG. 9A, the depicted embodiment is a non-cannulated fixation implant 900 having a head 910 and a distal tip 960 that are not cannulated, and the head 910 including a tool recess 920 for engaging a driving instrument, the implant also having exterior threading 940 and an open scaffold body 950 comprising a scaffold of random open and interconnected pores that is an engineered model based on the porous network of trabecular bone. Referring again to FIG. 9A, in the middle panel is a fixation implant 900 that is a variation of the fixation implant 900 shown above, wherein the shank 930 includes threading 940 along its length and only a portion of the length of the shank 930 is formed of the open scaffold body 950 and a portion of the shank 930 is a through solid 970. Referring to the bottom image of FIG. 9A, the depicted embodiment is a non-cannulated fixation implant 1000 having a head 1010 and a distal tip 1060 that are not cannulated, and the head 1010 including a tool recess 1020 for engaging a driving instrument, the implant also having exterior threading 1040 and a porous body 1050 comprising a framework of random open and interconnected pores that closely mimics the porous network of trabecular bone.

Figure 9B:
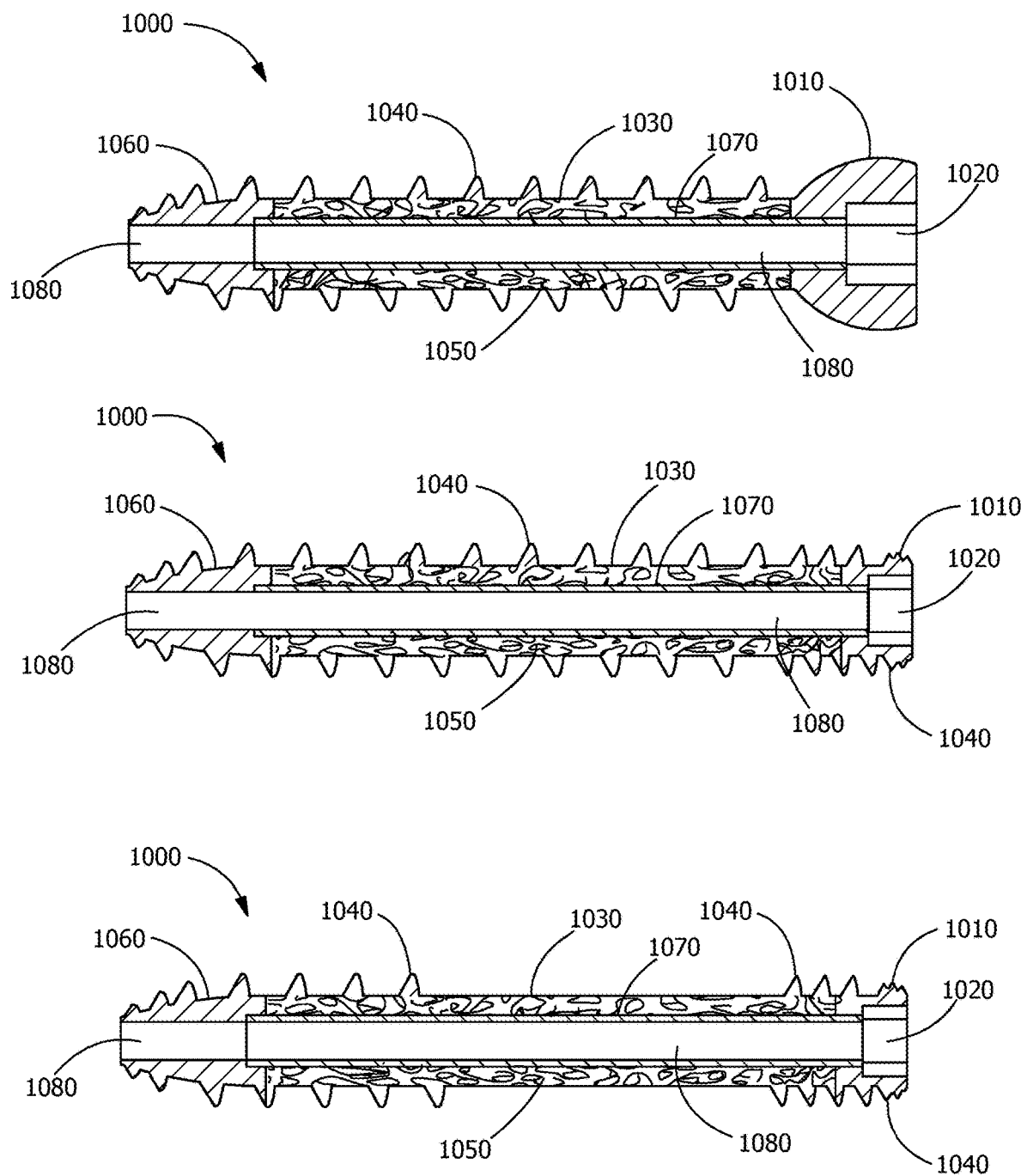
FIG. 9B shows three alternate embodiments of a fixation implant, the uppermost image depicting an cannulated implant having a solid-walled inner cylindrical through channel, the implant having exterior threading and an interior framework of random open and interconnected pores, shown in a side cross sectional view; the middle image depicting an cannulated implant having a solid-walled inner cylindrical through channel, the implant having a cylindrical head, exterior threading from the head to the distal tip and an interior framework of random open and interconnected pores, shown in a side cross sectional view; and, the third and bottom image depicting an cannulated implant having a solid-walled inner cylindrical through channel, the implant having a cylindrical head, exterior threading at the head and on a portion of the shank and at the distal tip and an interior framework of random open and interconnected pores, shown in a side cross sectional view.

Referring now to FIG. 9B, three alternate embodiments of a fixation implant are shown, each in a side cross sectional view. The uppermost image depicting a cannulated fixation implant 1000 having a solid-walled 1070 inner cylindrical through channel 1080, the implant 1000 having exterior threading 1040 and an interior framework of random open and interconnected pores. Referring again to FIG. 9B, the middle image depicts a cannulated implant 1000 having a solid-walled 1070 inner cylindrical through channel 1080, the implant having a cylindrical head 1010, exterior threading 1040 from the head 1010 to the distal tip 1060 and an interior framework of random open and interconnected pores, shown in a side cross sectional view. Referring again to FIG. 9B, the third and bottom image depicts a cannulated implant 1000 having a solid-walled 1070 inner cylindrical through channel 1080, the implant 1000 having a cylindrical head 1010, exterior threading 1040 at the head 1010 and on a portion of the shank 1030 and at the distal tip 1060 and an interior framework of random open and interconnected pores.

Referring now to FIG. 10-FIG. 16, each figure depicts an alternate embodiment of a fixation implant 2000, each in a side cross sectional view.

Figure 10:
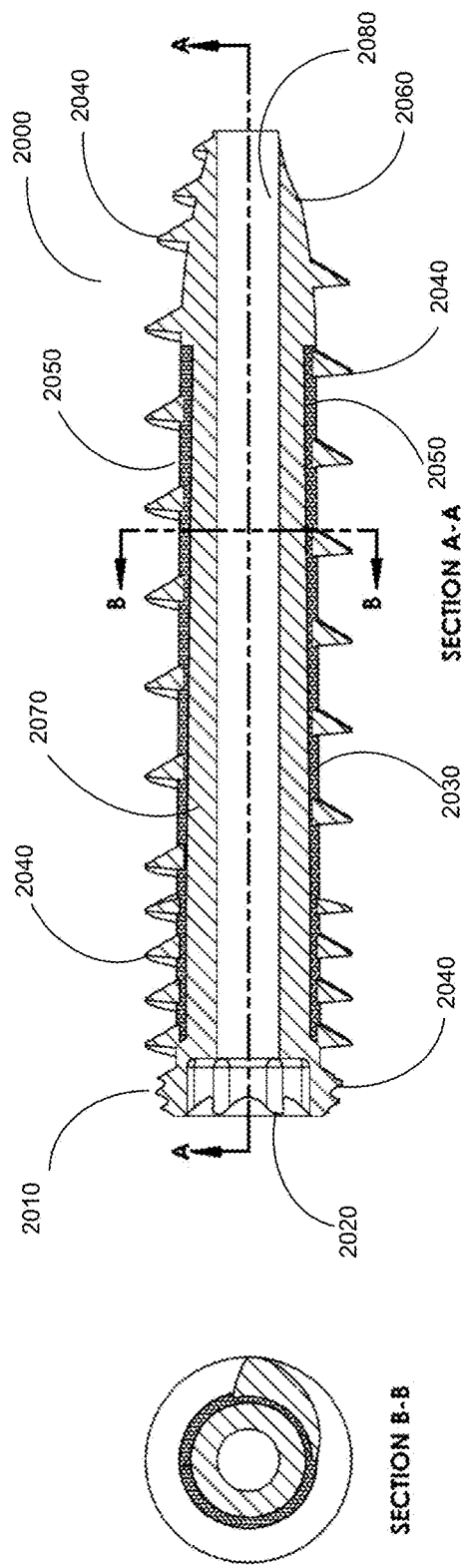
FIG. 10 shows an embodiment of a fixation implant in side cross sectional view that is cannulated with a solid-walled inner cylindrical through channel and an outer framework of random open and interconnected pores along a portion of the length of the shank, the outer framework of random open and interconnected pores bounded between the inner solid wall and an outer thread, and a threaded cylindrical head and threaded self-tapping distal tip each lacking an outer framework of random open and interconnected pores, each of the cylindrical head, the distal tip, the proximal portion of the shank and a central to distal portion of the shank having a different thread.

The implant 2000 of FIG. 10 is a headless type cannulated screw with a cylindrical threaded head 2010, a threaded self-tapping distal tip 2060, an inner cylindrical through channel 2080 with a solid inner wall 2070 and includes along a portion of the shank 2030 an outer framework of random open and interconnected pores 2050 that is between outer solid threads 2040 and the solid inner wall 2070. As shown, each of the head 2010, a proximal portion of the shank 2030, a central to distal portion of the shank 2030 and the distal tip 2060 each has a different thread. The head 2010 may include a tool recess 2020.

Figure 11:
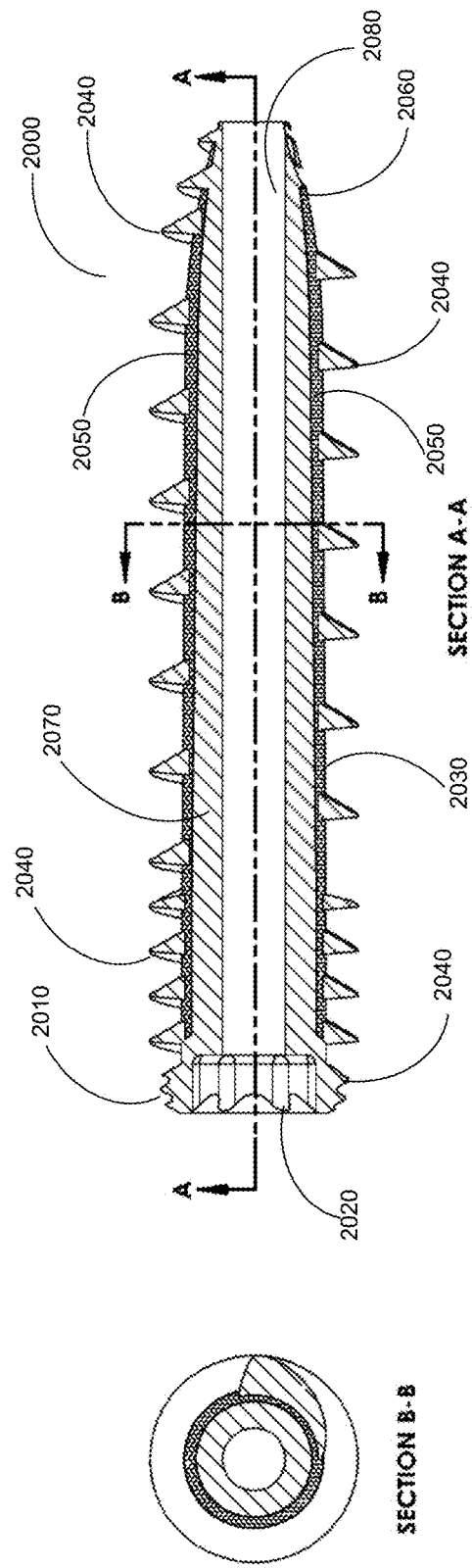
FIG. 11 shows an embodiment of a fixation implant in side cross sectional view that is cannulated with a solid-walled inner cylindrical through channel and an outer framework of random open and interconnected pores the length of a shank and the distal tip, the outer framework of random open and interconnected pores bounded between the inner solid wall and an outer thread, and a threaded cylindrical head lacking an outer framework of random open and interconnected pores, each of the cylindrical head, the distal tip, the proximal portion of the shank and a central to distal portion of the shank having a different thread.

The implant 2000 of FIG. 11 is a headless type cannulated screw with a cylindrical threaded head 2010, a threaded self-tapping distal tip 2060, an inner cylindrical through channel 2080 with a solid inner wall 2070 and includes along the shank 2030 from below the head 2010 to above the distal tip 2060 of the shank 2030 an outer framework of random open and interconnected pores 2050 that is between outer solid threads 2040 and the solid inner wall 2070. As shown, each of the head 2010, a proximal portion of the shank 2030, a central to distal portion of the shank 2030 and the distal tip 2060 has a different thread.

The implant 2000 of FIG. 12 is a headless type cannulated screw with a cylindrical threaded head 2010, a threaded self-tapping distal tip 2060, an inner cylindrical through channel 2080 with a wall formed of a framework of random open and interconnected pores 2050 along a portion of the length of the shank 2030, the outer framework of random open and interconnected pores 2050 bounded on the exterior by an outer solid thread. As shown, each of the head 2010, a proximal portion of the shank 2030, a central to distal portion of the shank 2030 and the distal tip 2060 has a different thread.

The implant 2000 of FIG. 13 headless type cannulated screw with a cylindrical threaded head 2010, a threaded self-tapping distal tip 2060, an inner cylindrical through channel 2080 with a solid inner wall 2070 and includes along a portion of the shank 2030 an outer framework of random open and interconnected pores 2050 that is between outer solid threads 2040 and the solid inner wall 2070. The shank 2030 includes along its length a series of circular and slotted fenestrations 3000 that extend from the exterior trough to the cannula. As shown, each of the head 2010, a proximal portion of the shank 2030, a central to distal portion of the shank 2030 and the distal tip 2060 has a different thread 2040.

The implant 2000 of FIG. 14 headless type cannulated screw with a cylindrical threaded head 2010, a threaded self-tapping distal tip 2060, an inner cylindrical through channel 2080 with a solid inner wall 2070 and includes along a portion of the shank 2030 an outer framework of random open and interconnected pores 2050 that is between outer solid threads 2040 and the solid inner wall 2070. As shown, each of the head 2010, a proximal portion of the shank 2030, a central to distal portion of the shank 2030 and the distal tip 2060 has a different thread, and the thread along the central to distal portion of the shank 2030 is interrupted and includes at least one short unthreaded portion 3100.

The implant 2000 of FIG. 15 headless type cannulated screw with a cylindrical threaded head 2010, a threaded self-tapping distal tip 2060, an inner cylindrical through channel 2080 with a solid center 2090, and includes along a portion of the shank 2030 an outer framework of random open and interconnected pores 2050 that is between outer solid threads 2040 and the solid interior. As shown, each of the head 2010, a proximal portion of the shank 2030, a central to distal portion of the shank 2030 and the distal tip 2060 has a different thread.

Figure 16:
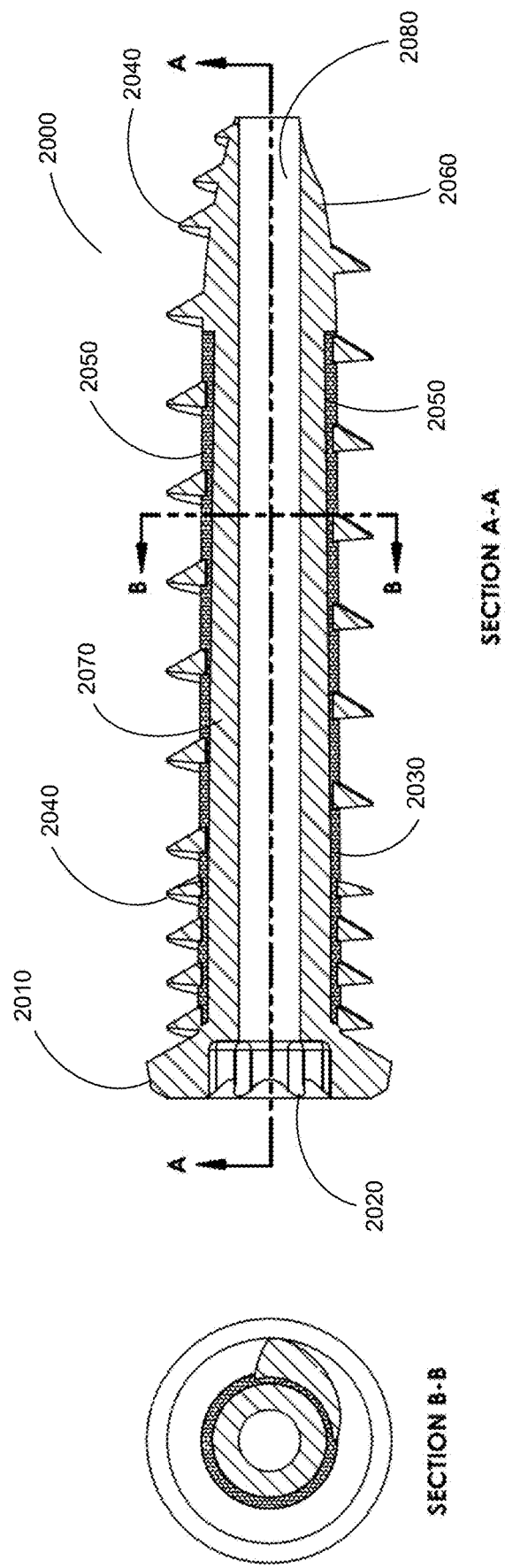
FIG. 16 shows an embodiment of a fixation implant in side cross sectional view that is cannulated with a solid-walled inner cylindrical through channel and an outer framework of random open and interconnected pores along a portion of the length of the shank, the outer framework of random open and interconnected pores bounded between the inner solid wall and an outer thread, and a non-threaded disc shaped head and threaded self-tapping distal tip each lacking an outer framework of random open and interconnected pores, each of the distal tip, the proximal portion of the shank and a central to distal portion of the shank having a different thread.

The implant 2000 of FIG. 16 is a cannulated screw with an unthreaded disc shaped head 2010, a threaded self-tapping distal tip 2060, an inner cylindrical through channel 2080 with a solid inner wall 2070 and includes along a portion of the shank 2030 an outer framework of random open and interconnected pores 2050 that is between outer solid threads 2040 and the solid inner wall 2070. As shown, each of the head 2010, a proximal portion of the shank 2030, a central to distal portion of the shank 2030 and the distal tip 2060 has a different thread.

With reference to some embodiments, the fixation implant 2000 includes a shank 2030 having a length from a proximal end to a distal end; a head 2010 that is integral with the shank 2030 at its proximal end and has a tool recess 2020 configured for engagement with a driving instrument; a tip 2060 that is integral with the shank 2030 at its distal end; and at least one thread extending along an external surface of the shank 2030. According to some embodiments, at least a portion of the shank 2030, or each of the shank 2030, the tip 2060, and the head 2010 have an open network body comprising a scaffold of open and interconnected pores 2050 mimicking a trabecular bone structure. According to some embodiments, the head 2010 has a headless configuration such that the head 2010 lacks an enlarged outer diameter relative to the shank 2030. According to some embodiments, at least a portion of the shank 2030 and the tip 2060 each have an open network body comprising a scaffold of open and interconnected pores 2050 mimicking a trabecular bone structure.

According to some embodiments, the head 2010 has a headless configuration such that the head 2010 lacks an enlarged outer diameter relative to the shank 2030.

According to some embodiments, the at least one thread 2040 is formed from metal and wherein the open network body comprising a framework of random open and interconnected pores 2050 is formed from at least one of a metal or a biocompatible polymer selected from the group consisting of: PEK, PEEK, PAEK, and combinations thereof.

According to some embodiments, the at least one thread 2040 is integral with a surface of the open network body comprising a scaffold of open and interconnected pores 2050.

According to some embodiments, the open network body comprising a scaffold of open and interconnected pores 2050 is exposed in gaps between the at least one thread.

According to some embodiments, at least a portion of the length shank 2030 is comprised of the open network body comprising a scaffold of open and interconnected pores 2050 without any solid center 2090 or inner cannulated solid wall 2070.

According to some embodiments, all of the shank 2030 is comprised of the open network body comprising a scaffold of open and interconnected pores 2050, and the shank 2030 may be cannulated.

According to some embodiments, all of the tip 2060 is comprised of the open network body comprising a scaffold of open and interconnected pores 2050.

According to some embodiments, the implant 2000 includes a cannula comprising an inner cylindrical through channel 2080 formed through at least a portion of the shank 2030. According to some such embodiments, the inner cylindrical through channel 2080 is formed through the fixation implant 2000 from and including the head 2010 through shank 2030 and to and including the tip 2060.

According to some embodiments, the shank 2030 is fenestrated.

According to some embodiments, a fixation implant 2000 includes a shank 2030 having a length from a proximal end to a distal end; a head 2010 that is integral with the shank 2030 at its proximal end and has a tool recess 2020 configured for engagement with a driving instrument; a tip 2060 that is integral with the shank 2030 at its distal end; and at least one thread extending along an external surface of the shank 2030. According to some embodiments, at least a portion of the shank 2030 has an open network body comprising a scaffold of open and interconnected pores 2050 mimicking a trabecular bone structure. According to some embodiments, the head 2010 has a headless configuration such that the head 2010 lacks an enlarged outer diameter relative to the shank 2030, and the tip 2060 and the head 2010 are non-porous and formed from solid material.

According to some embodiments, the shank 2030 is free from a cannula passing therethrough.

According to some embodiments, the shank 2030 is free of fenestrations 3000, the at least one thread is continuous from the head 2010 to the tip 2060, and the tip 2060 is self-tapping.

According to some embodiments, the at least one thread is interrupted by at least one short unthreaded portion along the shank 2030.

According to some embodiments, a fixation implant 2000 includes a cannula comprising an inner cylindrical through channel 2080 formed through at least a portion of the shank 2030, wherein the shank 2030 is free of fenestrations 3000. According to some embodiments, the shank 2030 is fenestrated.

According to some embodiments, the at least one thread is continuous from the head 2010 to the tip 2060, the tip 2060 is self-tapping, and the fixation implant 2000 further comprising a cannula comprising an inner cylindrical through channel 2080 formed through at least a portion of the shank 2030.

According to some embodiments, the shank 2030 is free of fenestrations 3000, the at least one thread is continuous from the head 2010 to the tip 2060, the tip 2060 is self-tapping, and the fixation implant 2000 further comprising a cannula comprising an inner cylindrical through channel 2080 formed through at least a portion of the shank 2030.

According to some embodiments, a fixation implant 2000 includes a shank 2030 having a length from a proximal end to a distal end; a head 2010 that is integral with the shank 2030 at its proximal end and has a tool recess 2020 configured for engagement with a driving instrument; a tip 2060 that is integral with the shank 2030 at its distal end; and at least one thread extending along an external surface of the shank 2030. According to some embodiments, at least a portion of the shank 2030 has an open network body comprising a scaffold of open and interconnected pores 2050 mimicking a trabecular bone structure, the head 2010 is a partially spherical head 2010 or flat, and the tip 2060 and the head 2010 are non-porous and formed from solid material.

In accordance with various embodiments, the open and porous open core of the fixation implant may be formed by any of a variety of processes, including additive (3D) manufacturing, conventional machining, and assembly of subparts, and in some embodiments, the open and porous open core of one or both the head and the shank are formed separately, wherein any threads on the fixation implant are formed from a material selected from metal, and the open core is separately formed using composite material that includes one or more of biocompatible polymers such as PEK, PEEK and PAEK, and other biodegradable polymers, bone material, BMP, and the like.

In some representative embodiments the fixation implant is or resembles a bone screw insofar as such fixation member includes a head and an elongated shank that includes a threaded portion, and in some embodiments, a shank portion that is proximate to the head that is not threaded. It will be appreciated that such fixation members may comprise one or more different thread features that may vary in any one or more number of threads, frequency, pitch, helix angle, thread angle, and major and minor diameters, and the threading may be male (extending away from the fixation implant), female (notches, grooves or channels cut into the fixation implant for receiving male threads), and combinations of these. A thread may be continuous or discontinuous. Further, any one or more of the thread features may be shaped as known in the art, including shapes selected from "V" shaped, square-, buttress-, reverse buttress threaded, and combinations of these, and the thread features may be left or right hand oriented, and the thread features may be self-cutting or self-tapping, or non-self-cutting or non-self-tapping, and combinations of these. Further, the threading may be present only on the shank, or may be present on the shank and one or more of at least a portion of the head and the distal tip. As described variously herein, a fixation member having external threading may alternately be referred to as a screw.

In yet other representative embodiments, the fixation implant is or resembles a bone anchor or plug insofar as such fixation member includes a head and an elongated shank that is only partially threaded. It will be appreciated that in some such embodiments, such fixation members may comprise one or more surface features for enhancing engagement with tissue such as cortical or cancellous bone, such features including, but not limited to, keels, fins, and distal bulbs or protuberances. In some embodiments, the fixation implant may have a surface treatment that is suitable for osseo-induction and may be one or more of porous and comprise an osseo-inductive agent, including a biological agent.

In accordance with some embodiments, the fixation member has an overall cylindrical, conical, or frustoconical shape that has either a fixed or an increasing diameter from distal to proximal. In some specific embodiments, the head has a frustoconical or a spherical or hemispherical shape, and in some embodiments, the shank has an overall or generally cylindrical shape with a tapered or conical distal tip. In various embodiments, the fixation member may have a shank that is fully threaded, or it may have a short-unthreaded portion.

As used herein, the term "head" in reference to the proximal head portion of the fixation implant means and includes a structure that is selected from spherical, shaped (e.g., generally spherical with one or more flats), hemi-spherical, frustoconical, discoid, and planar. Thus, in various embodiments with respect to the head, the fixation implant may resemble one of a conventional bone screw, a pedicle screw, a headless screw and other forms, wherein in each instance the head portion of the fixation implant is adapted with at least one feature for facilitating its insertion into bone. In accordance with some embodiments, a fixation member has a head that comprises a flat surface or top and may further comprise an enlarged outer diameter relative to the outer diameter of the shank, wherein the head may include an internal bore with one or more internal engagement features for receiving a driver. Such features may include one or more of a hex configuration for receiving a hex driver, or internal threading for receiving a threaded driver cap, or any of a variety of other possible engagement features. The head and shank of the fixation member, and any threaded driver cap may, in some embodiments, be cannulated for receiving a guide or k-wire there through.

Further still, in some embodiments, the fixation member may be cannulated, in some embodiments only a portion of the fixation member may be cannulated, and in some embodiments the fixation member is not cannulated.

In some such embodiments, the shape of the fixation member may be other than circular in cross section across the elongate axis, and thus the fixation member may have any one of a non-circular shape including ovoid and triangular. In some embodiments, all or only a portion of a fixation member may be circular in cross section and all or other portions of a fixation member may have a cross section that is other than circular, including ovoid and triangular. In some exemplary embodiments, a fixation member may have a frustoconical tip and a proximal adjacent portion that is triangular in cross section such that the tip can be pushed in to a bone hole. Further still, in some embodiments, the fixation member may have the same diameters shared for each of the head, shank and tip.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A pedicle screw, comprising:
a shank having a length from a proximal end to a distal end, a shank diameter that is continuous or tapered from the proximal end to the distal end, and a shank periphery along the length of the shank, the shank comprising a three-dimensional open network body along at least a portion of the length of the shank that allows communication through the three-dimensional open network body and 360 degrees around the shank to optimize complete bony integration when inserted in bone, wherein the three-dimensional open network body comprises at least one of: a scaffold of random open and interconnected pores formed along at least a central portion of the shank, at least one elongate helix formed along the entire length of the shank, or an organized or random arrangement of trusses formed along the entire length of the shank;
a partially spherical pedicle screw head that is monolithic with the shank at the proximal end of the shank, wherein at least a portion of the pedicle screw head includes the three-dimensional open network body;
a tip that is tapered relative to the shank and is integral with the shank at the shank's distal end; and
at least one solid thread extending along an external surface of the shank,
wherein the at least one solid thread and the three-dimensional open network body are formed from metal, and
wherein the at least one solid thread is integral with a surface of the three-dimensional open network body.

2. The pedicle screw of claim 1, wherein the scaffold of random open and interconnected pores mimic a trabecular bone structure.

3. The pedicle screw of claim 1, wherein the three-dimensional open network body is formed by a process selected from the group consisting of: additive (3D) manufacturing, conventional machining, assembly of subparts, and combinations thereof.

4. The pedicle screw of claim 1, wherein the at least one elongate helix includes a primary helix and a secondary helix defining a dual helical body.

5. The pedicle screw of claim 4, wherein the secondary helix is entwined with the primary helix, each helix having a different pitch.

6. The pedicle screw of claim 1, wherein the open network body comprises the organized arrangement of trusses.

7. The pedicle screw of claim 1, wherein the at least one solid thread includes:
a first solid thread having a first pitch extending along an external surface of the tip;
a second solid thread having a second pitch extending along a first portion of an external surface of the shank; and
a third solid thread having a third pitch extending along a second portion of the external surface of the shank.

8. The pedicle screw of claim 7, wherein:
the second portion of the external surface of the shank is disposed between the first portion of the external surface of the shank and the pedicle screw head;
the second pitch is greater than each of the first pitch and the third pitch;
the first solid thread is separated from the second solid thread by a first unthreaded portion of the shank;
the second solid thread is separated from the third solid thread by a second unthreaded portion of the shank; and
the pedicle screw head is unthreaded.

9. The pedicle screw of claim 1, wherein the shank includes the three-dimensional open network body along an entirety of the length of the shank.

10. The pedicle screw of claim 1, wherein when the three-dimensional open network body comprises the scaffold of random open and interconnected pores, the pedicle screw includes a solid-walled cannula formed through the shank, the pedicle screw head, and the tip, and the scaffold of random open and interconnected pores surrounds the solid-walled cannula.

11. The pedicle screw of claim 1, wherein when the three-dimensional open network body comprises the organized or random arrangement of trusses, the pedicle screw is not cannulated through the shank, the pedicle screw head, and the tip, and the shank includes a solid core and the organized or random arrangement of trusses surrounds the solid core.

12. The pedicle screw of claim 1, wherein when the three-dimensional open network body comprises the scaffold of random open and interconnected pores, the shank further includes a plurality of fenestrations selected from the group consisting of an opening, a slot, or a combination thereof around the periphery of the shank to further enhance bony ingrowth.

13. The pedicle screw of claim 1, wherein the shank diameter along at least the proximal end of the shank is approximately equal to a diameter of the pedicle screw head.

14. The pedicle screw of claim 1, wherein the shank diameter along at least the proximal end of the shank is smaller than a diameter of the pedicle screw head, and wherein the pedicle screw head is substantially spherical or hemispherical.

15. A pedicle screw comprising:
a shank having a length from a proximal end to a distal end;
a non-porous, partially spherical pedicle screw head that is monolithic with the shank at its proximal end, the non-porous pedicle screw head being formed from a solid material and comprising a tool recess configured for engagement with a driving instrument;
a tip that is integral with the shank at its distal end, the tip being non-porous and formed from a solid material; and
at least one non-porous thread formed along an external surface of the pedicle screw;
wherein a first portion of the shank adjacent the distal end includes a three-dimensional open network body comprising a scaffold of open and interconnected pores mimicking a trabecular bone structure that allows communication through the three-dimensional open network body and 360 degrees around the shank to optimize complete bony integration when inserted in bone, and wherein a second portion of the shank adjacent the proximal end is non-porous, wherein the at least one thread is continuous along a thread length of the pedicle screw from the tip into and over at least a portion of the second portion of the shank, wherein the at least one thread and the three-dimensional open network body are formed from metal, wherein the at least one thread is integral with a surface of the three-dimensional open network body, and wherein the three-dimensional open network body is exposed in gaps between the at least one thread.

16. A fixation implant comprising:

a shank having a length from a proximal end to a distal end;

a non-porous, partially spherical head that is monolithic with the shank at its proximal end, the partially spherical head being formed from a solid material and comprising a tool recess configured for engagement with a driving instrument;

a tip that is integral with the shank at its distal end, the tip being non-porous and formed from a solid material; and at least one non-porous thread formed along an external surface of the fixation implant;

wherein a first portion of the shank adjacent the distal end includes a three-dimensional open network body comprising a scaffold of open and interconnected pores mimicking a trabecular bone structure that allows communication through the three-dimensional open network body and 360 degrees around the shank to optimize complete bony integration when inserted in bone, and wherein a second portion of the shank adjacent the proximal end is non-porous, wherein the at least one thread is continuous along a thread length of the fixation implant from the tip into and over at least a portion of the second portion of the shank, wherein the at least one thread and the three-dimensional open network body are formed from metal, wherein the at least one thread is integral with a surface of the three-dimensional open network body, and wherein the three-dimensional open network body is exposed in gaps between the at least one thread.

17. The fixation implant of claim 16, wherein the three-dimensional open network body includes at least one additive material selected from the group consisting of polymers, biodegradable polymers, PEK, PEEK, PAEK, bone material, BMP, hydroxyapatite, and combinations thereof.

* * * * *